United States Patent
Zhang et al.

(10) Patent No.: US 10,271,797 B2
(45) Date of Patent: Apr. 30, 2019

(54) DETECTION OF WORSENING HEART FAILURE

(71) Applicant: Cardiac Pacemakers, Inc., St. Paul, MN (US)

(72) Inventors: Yi Zhang, Plymouth, MN (US); Pramodsingh Hirasingh Thakur, Woodbury, MN (US); Viktoria A. Averina, Shoreview, MN (US); Julie A. Thompson, Circle Pines, MN (US); Qi An, Blaine, MN (US); Jonathan Walter Krueger, New Richmond, WI (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 70 days.

(21) Appl. No.: 15/472,445

(22) Filed: Mar. 29, 2017

(65) Prior Publication Data

US 2017/0281096 A1    Oct. 5, 2017

Related U.S. Application Data

(60) Provisional application No. 62/316,939, filed on Apr. 1, 2016.

(51) Int. Cl.
*A61B 5/02* (2006.01)
*A61B 5/00* (2006.01)
(Continued)

(52) U.S. Cl.
CPC .......... *A61B 5/7275* (2013.01); *A61B 5/0031* (2013.01); *A61B 5/0402* (2013.01);
(Continued)

(58) Field of Classification Search
CPC ... A61B 5/0031; A61B 5/0215; A61B 5/0402; A61B 5/0538; A61B 5/11; A61B 5/4836;
(Continued)

(56) References Cited

U.S. PATENT DOCUMENTS

2010/0179409 A1* 7/2010 Kamath ............. A61B 5/14865
600/365

FOREIGN PATENT DOCUMENTS

| WO | WO-2009109766 A1 | 9/2009 |
| WO | WO-2010024738 A1 | 3/2010 |

(Continued)

OTHER PUBLICATIONS

Cowie, Martin R., et al., "Development and validation of an integrated diagnostic algorithm derived from parameters monitored in implantable devices for identifying patients at risk for heart failure hospitalization in an ambulatory setting", European Heart Journal Advance Access, (Mar. 19, 2013), 1-9.

(Continued)

*Primary Examiner* — George Manuel
(74) *Attorney, Agent, or Firm* — Schwegman Lundberg & Woessner, P.A.

(57) ABSTRACT

Systems and methods for detecting a target cardiac condition such as events indicative of worsening heart failure are described. A system may include sensor circuits for sensing physiological signals and a signal processor for generating a predictor trend indicative of temporal change of the physiological signal. The predictor trend may be transformed into a sequence of transformed indices using a codebook that includes a plurality of threshold pairs each including onset and reset thresholds. The codebook may be constructed and updated using physiological data. The system may detect target cardiac condition using the transformed indices.

20 Claims, 11 Drawing Sheets

(51) Int. Cl.

| | |
|---|---|
| *A61B 5/0402* | (2006.01) |
| *A61B 5/11* | (2006.01) |
| *A61N 1/365* | (2006.01) |
| *A61N 1/39* | (2006.01) |
| *G06F 19/00* | (2018.01) |
| *G16H 40/63* | (2018.01) |
| *G16H 50/20* | (2018.01) |
| *A61B 5/0215* | (2006.01) |
| *A61B 5/053* | (2006.01) |

(52) U.S. Cl.
CPC .............. *A61B 5/11* (2013.01); *A61B 5/4836* (2013.01); *A61B 5/7253* (2013.01); *A61N 1/365* (2013.01); *A61N 1/3956* (2013.01); *A61N 1/3987* (2013.01); *G06F 19/00* (2013.01); *G06F 19/325* (2013.01); *G16H 40/63* (2018.01); *G16H 50/20* (2018.01); *A61B 5/0215* (2013.01); *A61B 5/0538* (2013.01)

(58) Field of Classification Search
CPC .... A61B 5/7253; A61B 5/7275; A61N 1/365; A61N 1/3956; A61N 1/3987; G06F 19/00; G06F 19/325; G16H 40/63; G16H 50/20
See application file for complete search history.

(56) References Cited

FOREIGN PATENT DOCUMENTS

| | | |
|---|---|---|
| WO | WO-2015065674 A1 | 5/2015 |
| WO | WO-2017172864 A1 | 10/2017 |

OTHER PUBLICATIONS

Thakur, Pramodsingh Hirasingh, et al., "Predictions of Worsening Heat Failure", U.S. Appl. No. 62/236,416, filed Oct. 2, 2015.

Whellan, David J., et al., "Combined Head Failure Device Diagnostics Identify Patients at Higher Risk of Subsequent Heart Failure Hospitalizations", Journal of the American College of Cardioiogy, vol. 55, No. 17, (2010), 1803-1810.

"International Application Serial No. PCT/US2017/024671, International Preliminary Report on Patentability dated Oct. 11, 2018", 8 pgs.

"International Application Serial No. PCT/US2017/024671, International Search Report dated Jun. 14, 2017", 4 pgs.

"International Application Serial No. PCT/US2017/024671, Written Opinion dated Jun. 14, 2017", 6 pgs.

* cited by examiner

DETECTION OF WORSENING HEART FAILURE

CLAIM OF PRIORITY

This application claims the benefit of priority under 35 U.S.C. § 119(e) of U.S. Provisional Patent Application Ser. No. 62/316,939, filed on Apr. 1, 2016, which is herein incorporated by reference in its entirety.

TECHNICAL FIELD

This document relates generally to medical devices, and more particularly, to systems, devices and methods for detecting and monitoring events indicative of worsening of congestive heart failure.

BACKGROUND

Congestive heart failure (CHF or HF) is a major health problem and affects many people in the United States alone. CHF patients may have enlarged heart with weakened cardiac muscles, resulting in poor cardiac output of blood. Although CHF is usually a chronic condition, it may occur suddenly. It may affect the left heart, right heart or both sides of the heart. If CHF affects the left ventricle, signals that control the left ventricular contraction are delayed, and the left and right ventricles do not contract simultaneously. Non-simultaneous contractions of the left and right ventricles further decrease the pumping efficiency of the heart.

In many CHF patients, elevated pulmonary vascular pressures may cause fluid accumulation in the lungs over time. The fluid accumulation may precede or coincide with worsening of HF such as episodes of HF decompensation. The HF decompensation may be characterized by pulmonary or peripheral edema, reduced cardiac output, and symptoms such as fatigue, shortness of breath, and the like.

OVERVIEW

Frequent monitoring of CHF patients and timely detection of events indicative of worsening HF (WHF) may reduce cost associated with HF hospitalization. Identification of patient at an elevated risk of developing future WHF events may help ensure timely treatment, improve the prognosis and patient outcome, and avoid unnecessary medical intervention and reduce healthcare cost.

Ambulatory medical devices may be used for monitoring HF patient and detecting WHF events. Examples of such ambulatory medical devices may include implantable medical devices (IMD), subcutaneous medical devices, wearable medical devices or other external medical devices. The ambulatory medical devices may include physiological sensors which may be configured to sense electrical activity and mechanical function of the heart. The ambulatory medical devices may deliver therapy such as electrical stimulations to target tissues or organs, such as to restore or improve the cardiac function. Some of these devices may provide diagnostic features, such as using transthoracic impedance or other sensor signals to detect a disease or a disease condition. For example, fluid accumulation in the lungs decreases the transthoracic impedance due to the lower resistivity of the fluid than air in the lungs.

Detection of a WHF event, such as a precipitating event such as increased thoracic fluid accumulation, may be based on a detected change of a sensor signal (such as a thoracic impedance signal) from a reference signal. An ideal detector of a WHF event, such as a HF decompensation event, may have one or more of a high sensitivity, a high specificity, a low false positive rate (FPR), or a high positive predictive value (PPV). The sensitivity may be represented as a percentage of actual HF decompensation episodes that are correctly recognized by a detection method. The specificity may be represented as a percentage of actual non-WHF events or time periods free of WHF events that are correctly recognized as non-WHF events or time periods free of WHF events by the detection method. The FPR may be represented as a frequency of false positive detections of WHF events per patient within a specified time period (e.g., a year). The PPV may be represented as a percentage of the detected WHF events, as declared by the detection method, which are actual WHF events. A high sensitivity may help ensure timely intervention to a patient with an impending WHF event, whereas a high specificity and a high PPV may help avoid unnecessary intervention and added healthcare cost due to false alarms.

The WHF event may be detected using multiple physiological sensors. Signals sensed from multiple sensor signals are usually not easily comparable or combined. This may be due to the fact that the various physiological sensors have different physical properties, sensing modalities, or operating characteristics. Consequently, the signals sensed from the various sensors may have different signal properties such as signal dynamic range, responsiveness to a physiological or non-physiological event (including signal change or rate of change), or signal qualities such as signal-to-noise ratio (SNR). To account for such inter-signal differences, detection parameters such as detection threshold generally may be individually determined or adjusted for each physiological signal. However, such an approach may not be ideal for a multi-sensor based WHF detection system or process, as it may not only increase the complexity and the operation cost, but may also reduce data interpretability (e.g., correspondence between a clinical observation of worsening heart failure and the degree of signal changes across the sensor signals) and thus impacts user experience in healthcare professional managing the HF patient. Moreover, individually adjusted thresholds do not mitigate the lack of comparability across sensor signals or the complexity of combining various sensor signals.

Embodiments of the present subject matter provide systems, devices, and methods for detecting worsening cardiac condition such as a WHF event. The present subject matter includes a system for sensing physiological signals and generating a predictor trend indicative of temporal change of the physiological signal. The predictor trend may be transformed into a sequence of transformed indices using a codebook that includes a plurality of threshold pairs each including onset and reset thresholds. The codebook may be constructed and updated using physiological data. The system may detect the target physiological event using the transformed indices.

In Example 1, a system for detecting a target physiological event is disclosed. The system may comprise a physiological sensor circuit that includes a sense amplifier circuit to sense a first physiological signal, a signal processor circuit coupled to the physiological sensor circuit, and a detector circuit coupled to the signal processor circuit. The signal processor circuit may include a predictor circuit to generate a first predictor trend using the first physiological signal, the first predictor trend indicating a change of the first physiological signal over time. The signal processor circuit may include a signal transformation circuit to transform the first predictor trend into transformed indices using a first plurality of threshold pairs each including an onset threshold and a reset threshold. The detector circuit may detect the target physiological event using the transformed indices.

Example 2 may include, or may optionally be combined with the subject matter of Example 1 to optionally include, an output circuit to generate a human-perceptible alert in response to the transformed indices satisfying a detection criterion.

Example 3 may include, or may optionally be combined with the subject matter of Example 1 to optionally include, the signal transformation circuit that may transform the first predictor trend using a codebook including an association between the first plurality of threshold pairs and corresponding code words. The transformation of the first predictor trend using the codebook may include includes, for a specified portion of the first predictor trend: identifying from the codebook a relevant threshold pair with corresponding onset and reset thresholds, the specified portion temporally occurring after the first predictor trend exceeding the corresponding onset threshold and prior to the first predictor trend subsequently falling below the reset threshold; and assigning a numerical code corresponding to the identified relevant threshold pair to the specified portion of the first predictor trend.

Example 4 may include, or may optionally be combined with the subject matter of Example 3 to optionally include, the signal transformation circuit that may identify from the codebook two or more relevant threshold pairs for the specified portion of the first predictor trend, determine a dominant threshold pair from the two or more relevant threshold pairs, where the dominant threshold pair may have a larger onset threshold or a larger reset threshold than any other of the identified relevant threshold pairs, and assign a numerical code corresponding to the dominant threshold pair to the specified portion of the first predictor trend.

Example 5 may include, or may optionally be combined with the subject matter of Example 3 to optionally include, the code words that may include numerical codes within a specified range. The threshold pair with a higher onset threshold or a higher reset threshold corresponds to a larger numerical code than a threshold pair with a lower onset threshold or a lower reset threshold.

Example 6 may include, or may optionally be combined with the subject matter of Example 3 to optionally include, a codebook formation circuit that may produce a receiver operating characteristic (ROC) using detections of the target physiological event according to a plurality of candidate threshold pairs, the ROC including operating points indicating sensitivity statistics and false positive rate (FPR) statistics associated with the plurality of candidate threshold pairs. The codebook formation circuit may partition the ROC into a plurality of ROC segments defined by boundary operating points associated with respective boundary threshold pairs, assign code words for the partitioned ROC segments, and generate the codebook including the mapping between the boundary threshold pairs and the code words.

Example 7 may include, or may optionally be combined with the subject matter of Example 6 to optionally include, the partition of the ROC that may include sampling the FPR statistics within a specified FPR range at specified sampling intervals, sampling the sensitivity statistics within a specified sensitivity range at specified sampling intervals, or sampling a specified portion of the operation points within a specified sensitivity range and a specified FPR range at specified sampling intervals.

Example 8 may include, or may optionally be combined with the subject matter of Example 7 to optionally include, the codebook formation circuit that may sample from the specified portion of the operation points a specified number of operating points equally spaced along the specified portion of the operation points according to a distance measure.

Example 9 may include, or may optionally be combined with the subject matter of Example 3 to optionally include, the signal transformation circuit that may produce a signal intensity distribution (SID) of the first predictor trend, and transform the first predictor trend using the codebook and the SID of the first predictor trend. The SID may represent percentile frequencies of the first predictor trend across a plurality of candidate onset or reset thresholds. The codebook may include an association between the first plurality of threshold pairs including a plurality of percentile frequency thresholds (PFTs) and corresponding code words.

Example 10 may include, or may optionally be combined with the subject matter of Example 3 to optionally include, a codebook formation circuit that may be configured to receive a plurality of first predictor trends from a plurality of patients, produce a composite signal intensity distribution (cSID) of the plurality of first predictor trends where the cSID represents percentile frequencies across plurality of candidate onset or reset thresholds, partition the cSID into a plurality of distribution segments defined by boundary percentile frequencies associated with respective boundary onset or reset thresholds, assign code words for the partitioned distribution segments, and generate the codebook including the mapping between the boundary onset or reset thresholds and the code words.

Example 11 may include, or may optionally be combined with the subject matter of Example 10 to optionally include, the partition of the cSID that may include sampling the candidate onset or reset thresholds within a specified threshold range at specified sampling intervals, or sampling the percentile frequencies within a specified percentile frequency range at specified sampling intervals.

Example 12 may include, or may optionally be combined with the subject matter of Example 10 to optionally include, the partition of the cSID that may include receiving one or more anchor percentile frequencies (APFs), partitioning the cSID into a plurality of distribution segments using the APFs wherein the partitioned distribution segments are associated with respective percentile frequency ranges and onset or rest threshold ranges, and sampling the candidate onset or reset thresholds within each of the onset or reset threshold range.

Example 13 may include, or may optionally be combined with the subject matter of Example 10 to optionally include, the codebook formation circuit that may be configured to generate the boundary reset thresholds as a function of the boundary onset thresholds.

Example 14 may include, or may optionally be combined with the subject matter of Example 1 to optionally include, the physiological sensor circuit that may sense a second physiological signal, the predictor circuit that may generate a second predictor trend different from the first predictor trend using the second physiological signal, the signal transformation circuit that may transform the first and second predictor trends jointly into the transformed indices according to a codebook, and the detector circuit that may detect the target physiological event using the transformed indices. The codebook may include an association between a plurality of multi-dimensional thresholds and a plurality of code words, each multi-dimensional threshold including a first threshold pair for the first predictor trend and a second threshold pair for the second predictor trend.

Example 15 may include, or may optionally be combined with the subject matter of Example 1 to optionally include, the predictor circuit that may generate a signal metric trend from the first physiological signal, and generate the first predictor trend using a comparison between a first portion of the signal metric trend within a short-term time window and a second portion of the signal metric trend within a long-term time window longer in duration than the short-term window.

In Example 16, a method for detecting a target physiological event in a patient is disclosed. The method may include steps of: sensing a first physiological signal; processing the first physiological signal to generate a first predictor trend indicating a change of the first physiological signal over time; transforming the first predictor trend into transformed indices using a first plurality of threshold pairs each including an onset threshold and a reset threshold; and detecting the target physiological event using the transformed indices.

Example 17 may include, or may optionally be combined with the subject matter of Example 16 to optionally include, the method of transforming the first predictor trend that may include, for a specified portion of the first predictor trend: identifying from a codebook a relevant threshold pair with corresponding onset and reset thresholds, the specified portion temporally occurring after the first predictor trend exceeding the corresponding onset threshold and prior to the first predictor trend subsequently falling below the reset threshold; and assigning a numerical code corresponding to the identified relevant threshold pair to the specified portion of the first predictor trend. The codebook includes an association between the first plurality of threshold pairs and corresponding code words, the code words including numerical codes within a specified range.

Example 18 may include, or may optionally be combined with the subject matter of Example 17 to optionally include, the step of transforming the first predictor trend that may further include, for the specified portion of the first predictor trend: identifying from the codebook two or more relevant threshold pairs; determining from the two or more relevant threshold pairs a dominant threshold pair having a larger onset threshold or a larger reset threshold than any other of the identified relevant threshold pairs; and assigning a numerical code corresponding to the dominant threshold pair to the specified portion of the first predictor trend.

Example 19 may include, or may optionally be combined with the subject matter of Example 17 to optionally include, a step of generating a codebook which may include: producing a receiver operating characteristic (ROC) using detections of the target physiological event according to a plurality of candidate threshold pairs, the ROC including operating points indicating sensitivity statistics and false positive rate (FPR) statistics associated with the plurality of candidate threshold pairs; partitioning the ROC into a plurality of ROC segments defined by boundary operating points associated with respective boundary threshold pairs; assigning code words for the partitioned ROC segments; and generating a mapping between the boundary threshold pairs and the code words.

Example 20 may include, or may optionally be combined with the subject matter of Example 19 to optionally include, the partitioning the ROC that may include sampling the FPR statistics within a specified FPR range at specified sampling intervals, sampling the sensitivity statistics within a specified sensitivity range at specified sampling intervals, or sampling a specified portion of the operation points within a specified sensitivity range and a specified FPR range at specified sampling intervals.

Example 21 may include, or may optionally be combined with the subject matter of Example 17 to optionally include, a step of generating a codebook that includes: producing a composite signal intensity distribution (cSID) using a plurality of first predictor trends from a plurality of patients, the cSID representing percentile frequencies across plurality of candidate onset or reset thresholds; partitioning the cSID into a plurality of distribution segments defined by boundary percentile frequencies associated with respective boundary onset or reset thresholds; assigning code words for the partitioned distribution segments; and generating a mapping between the boundary onset or reset thresholds and the code words.

Example 22 may include, or may optionally be combined with the subject matter of Example 21 to optionally include, the partitioning of the cSID that may include sampling the candidate onset or reset thresholds within a specified threshold range at specified sampling intervals, or sampling the percentile frequencies within a specified percentile frequency range at specified sampling intervals.

Example 23 may include, or may optionally be combined with the subject matter of Example 16 to optionally include, steps of sensing a second physiological signal, processing the second physiological signal to generate a second predictor trend different from the first predictor trend, and transforming the first and second predictor trends jointly into the transformed indices according to a codebook. The codebook may include an association between a plurality of multi-dimensional thresholds and a plurality of code words, each multi-dimensional threshold including a first threshold pair for the first predictor trend and a second threshold pair for the second predictor trend. The detection of the target physiological event may include detecting the target physiological event using the transformed indices.

The systems, devices, and methods discussed in this document may improve the medical technology of automated monitoring of patients with worsening heart failure (WHF). Detection of WHF based on signal transformation using a codebook may enhance the performance and functionality of a medical system or an ambulatory medical device for detecting WHF. In certain examples, the enhanced device functionality may include more efficient comparison or combination of signals sensed from multiple sensors, along with reduced system complexity and operation cost. This in turn may allow for more timely and accurate detection of WHF (e.g., lower false positive rate and higher positive predictive value), and reduce healthcare costs associated with management and hospitalization of heart failure patients. The data transformation as discussed in this document may also enhance data interpretability, thereby improving the user experience in heart failure patient management. Additionally, the systems, devices, and methods discussed in this document allows for more efficient device memory usage, such as by storing transformed signal indices with improved inter-sensor comparability and therefore clinically more relevant to WHF detection. As fewer false positive detections are provided, device battery life can be extended, fewer unnecessary drugs and procedures may be scheduled, prescribed, or provided, and an overall system cost savings may be realized.

This Overview is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Disclosed herein are systems, devices, and methods for detecting one or more target physiological events or conditions. The events may include early precursors of a HF decompensation episode. That is, these events may occur well before the systematic manifestation of worsening of HF. Therefore, by detecting the precursor events, the present subject matter may provide a method and device for detecting an impending HF decompensation episode. The systems, devices, and methods described herein may be used to determine cardiac condition such as HF status and/or track progression of the cardiac condition such as worsening of or recovery from a HF event. This system may also be used in the context of other diseases associated with accumulation of thoracic fluid, such as pneumonia.

Figure 1:
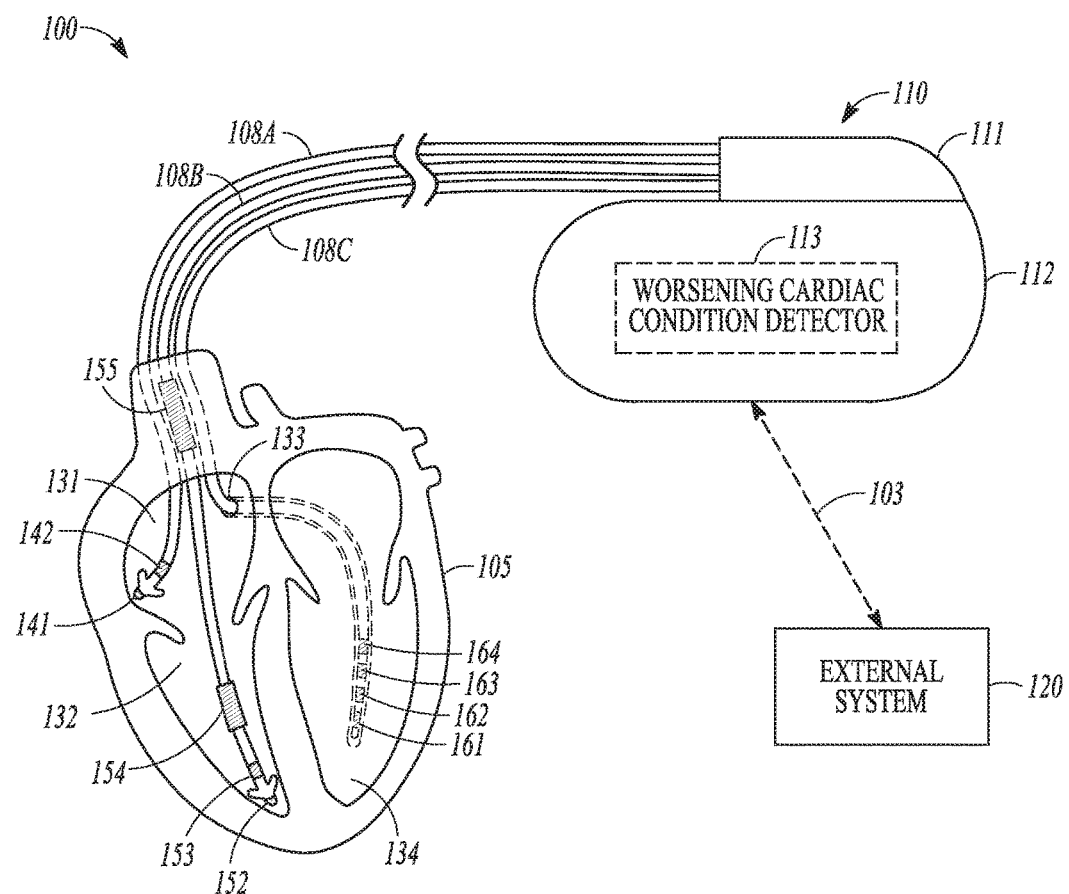
FIG. 1 illustrates generally an example of a cardiac rhythm management (CRM) system and portions of the environment in which the CRM system operates.

FIG. 1 illustrates generally an example of a Cardiac Rhythm Management (CRM) system 100 and portions of an environment in which the CRM system 100 may operate. The CRM system 100 may include an ambulatory medical device, such as an implantable medical device (IMD) 110 that may be electrically coupled to a heart 105 such as through one or more leads 108A-C, and an external system 120 that may communicate with the IMD 110 such as via a communication link 103. The IMD 110 may include an implantable cardiac device such as a pacemaker, an implantable cardioverter-defibrillator (ICD), or a cardiac resynchronization therapy defibrillator (CRT-D). In some examples, the CRM system may include a subcutaneously implanted device, a wearable external device, a neural stimulator, a drug delivery device, a biological therapy device, or one or more other ambulatory medical devices. The IMD 110 may be coupled to, or may be substituted by a monitoring medical device such as a bedside or other external monitor.

As illustrated in FIG. 1, the IMD 110 may include a hermetically sealed can housing 112 that may house an electronic circuit that may sense a physiological signal in the heart 105 and may deliver one or more therapeutic electrical pulses to a target region, such as in the heart, such as through one or more leads 108A-C. The CRM system 100 may include only one lead such as 108B, or may include two leads such as 108A and 108B.

The lead 108A may include a proximal end that may be configured to be connected to IMD 110 and a distal end that may be configured to be placed at a target location such as in the right atrium (RA) 131 of the heart 105. The lead 108A may have a first pacing-sensing electrode 141 that may be located at or near its distal end, and a second pacing-sensing electrode 142 that may be located at or near the electrode 141. The electrodes 141 and 142 may be electrically connected to the IMD 110 such as via separate conductors in the lead 108A, such as to allow for sensing of the right atrial activity and optional delivery of atrial pacing pulses. The lead 108B may be a defibrillation lead that may include a proximal end that may be connected to IMD 110 and a distal end that may be placed at a target location such as in the right ventricle (RV) 132 of heart 105. The lead 108B may have a first pacing-sensing electrode 152 that may be located at distal end, a second pacing-sensing electrode 153 that may be located near the electrode 152, a first defibrillation coil electrode 154 that may be located near the electrode 153, and a second defibrillation coil electrode 155 that may be located at a distance from the distal end such as for superior vena cava (SVC) placement. The electrodes 152 through 155 may be electrically connected to the IMD 110 such as via separate conductors in the lead 108B. The electrodes 152 and 153 may allow for sensing of a ventricular electrogram and may allow delivery of one or more ventricular pacing pulses, and electrodes 154 and 155 may allow for delivery of one or more ventricular cardioversion/defibrillation pulses. In an example, the lead 108B may include only three electrodes 152, 154 and 155. The electrodes 152 and 154 may be used for sensing or delivery of one or more ventricular pacing pulses, and the electrodes 154 and 155 may be used for delivery of one or more ventricular cardioversion or defibrillation pulses. The lead 108C may include a proximal end that may be connected to the IMD 110 and a distal end that may be configured to be placed at a target location such as in a left ventricle (LV) 134 of the heart 105. The lead 108C may be implanted through the coronary sinus 133 and may be placed in a coronary vein over the LV such as to allow for delivery of one or more pacing pulses to the LV. The lead 108C may include an electrode 161 that may be located at a distal end of the lead 108C and another electrode 162 that may be located near the electrode 161. The electrodes 161 and 162 may be electrically connected to the IMD 110 such as via separate conductors in the lead 108C such as to allow for sensing of the LV electrogram and allow delivery of one or more resynchronization pacing pulses from the LV. Additional electrodes may be included in or along the lead 108C. In an example, as illustrated in FIG. 1, a third electrode 163 and a fourth electrode 164 may be included in the lead 108. In some examples (not shown in FIG. 1), at least one of the leads 108A-C, or an additional lead other than the leads 108A-C, may be implanted under the skin surface without being within at least one heart chamber, or at or close to heart tissue.

The IMD 110 may include an electronic circuit that may sense a physiological signal. The physiological signal may include an electrogram or a signal representing mechanical function of the heart 105. The hermetically sealed can housing 112 may function as an electrode such as for sensing or pulse delivery. For example, an electrode from one or more of the leads 108A-C may be used together with the can housing 112 such as for unipolar sensing of an electrogram or for delivering one or more pacing pulses. A defibrillation electrode from the lead 108B may be used together with the can housing 112 such as for delivering one or more cardioversion/defibrillation pulses. In an example, the IMD 110 may sense impedance such as between electrodes located on one or more of the leads 108A-C or the can housing 112. The IMD 110 may be configured to inject current between a pair of electrodes, sense the resultant voltage between the same or different pair of electrodes, and determine impedance using Ohm's Law. The impedance may be sensed in a bipolar configuration in which the same pair of electrodes may be used for injecting current and sensing voltage, a tripolar configuration in which the pair of electrodes for current injection and the pair of electrodes for voltage sensing may share a common electrode, or tetrapolar configuration in which the electrodes used for current injection may be distinct from the electrodes used for voltage sensing. In an example, the IMD 110 may be configured to inject current between an electrode on the RV lead 108B and the can housing 112, and to sense the resultant voltage between the same electrodes or between a different electrode on the RV lead 108B and the can housing 112. A physiological signal may be sensed from one or more physiological sensors that may be integrated within the IMD 110. The IMD 110 may also be configured to sense a physiological signal from one or more external physiological sensors or one or more external electrodes that may be coupled to the IMD 110. Examples of the physiological signal may include one or more of thoracic impedance, intracardiac impedance, arterial pressure, pulmonary artery pressure, RV pressure, LV coronary pressure, coronary blood temperature, blood oxygen saturation, one or more heart sounds, physical activity or exertion level, posture, respiration, body weight, or body temperature.

The arrangement and functions of these leads and electrodes are described above by way of example and not by way of limitation. Depending on the need of the patient and the capability of the implantable device, other arrangements and uses of these leads and electrodes are contemplated.

As illustrated, the CRM system 100 may include a worsening cardiac condition detector 113. The worsening cardiac condition detector 113 may receive a physiological signal, such as sensed from the patient using the electrodes on one or more of the leads 108A-C or the can housing 112, or other physiological sensors deployed on or within the patient and communicated with the IMD 110. Examples of the physiological signals may include impedance signal, thoracic impedance signal, heart sounds signal, intracardiac or endocardial acceleration signals, pressure signals, respiration signal, and activity signal, among others. The worsening cardiac condition detector 113 may generate a signal metric from the received physiological signal and further generate a predictor trend using the first signal metric, such as a periodically or continuously accumulated deviations from a reference signal level. The worsening cardiac condition detector 113 may include a signal transformation module to transform the predictor trend using a plurality of threshold pairs each including an onset threshold and a reset threshold. The worsening cardiac condition detector 113 may detect a target physiological event such as a WHF event using the transformed predictor trend. Examples of the worsening cardiac condition detector 113 are described below, such as with reference to FIG. 2.

The external system 120 may allow for programming of the IMD 110 and may receive information about one or more signals acquired by IMD 110, such as may be received via a communication link 103. The external system 120 may include a local external IMD programmer. The external system 120 may include a remote patient management system that may monitor patient status or adjust one or more therapies such as from a remote location.

The communication link 103 may include one or more of an inductive telemetry link, a radio-frequency telemetry link, or a telecommunication link, such as an internet connection. The communication link 103 may provide for data transmission between the IMD 110 and the external system 120. The transmitted data may include, for example, real-time physiological data acquired by the IMD 110, physiological data acquired by and stored in the IMD 110, therapy history data or data indicating IMD operational status stored in the IMD 110, one or more programming instructions to the IMD 110 such as to configure the IMD 110 to perform one or more actions that may include physiological data acquisition such as using programmably specifiable sensing electrodes and configuration, device self-diagnostic test, or delivery of one or more therapies.

The worsening cardiac condition detector 113, although illustrated in FIG. 1 as being implemented in the IMD 110, may alternatively be implemented in a subcutaneously implanted device, a wearable external device, a neural stimulator, a drug delivery device, a biological therapy device, or one or more diagnostic devices. In some examples, the worsening cardiac condition detector 113 may be implemented in the external system 120. The external system 120 may be configured to perform WHF event detection such as using data extracted from the IMD 110 or data stored in a memory within the external system 120. In an example, portions of the worsening cardiac condition detector 113 may be distributed between the IMD 110 and the external system 120.

Portions of the IMD 110 or the external system 120 may be implemented using hardware, software, or any combination of hardware and software. Portions of the IMD 110 or the external system 120 may be implemented using an application-specific circuit that may be constructed or configured to perform one or more particular functions, or may be implemented using a general-purpose circuit that may be programmed or otherwise configured to perform one or more particular functions. Such a general-purpose circuit may include a microprocessor or a portion thereof, a microcontroller or a portion thereof, or a programmable logic circuit, or a portion thereof. For example, a "comparator" may include, among other things, an electronic circuit comparator that may be constructed to perform the specific function of a comparison between two signals or the comparator may be implemented as a portion of a general-purpose circuit that may be driven by a code instructing a portion of the general-purpose circuit to perform a comparison between the two signals. While described with reference to the IMD 110, the CRM system 100 could include a subcutaneous medical device (e.g., subcutaneous ICD, subcutaneous diagnostic device), wearable medical devices (e.g., patch based sensing device), or other external medical devices.

Figure 2:
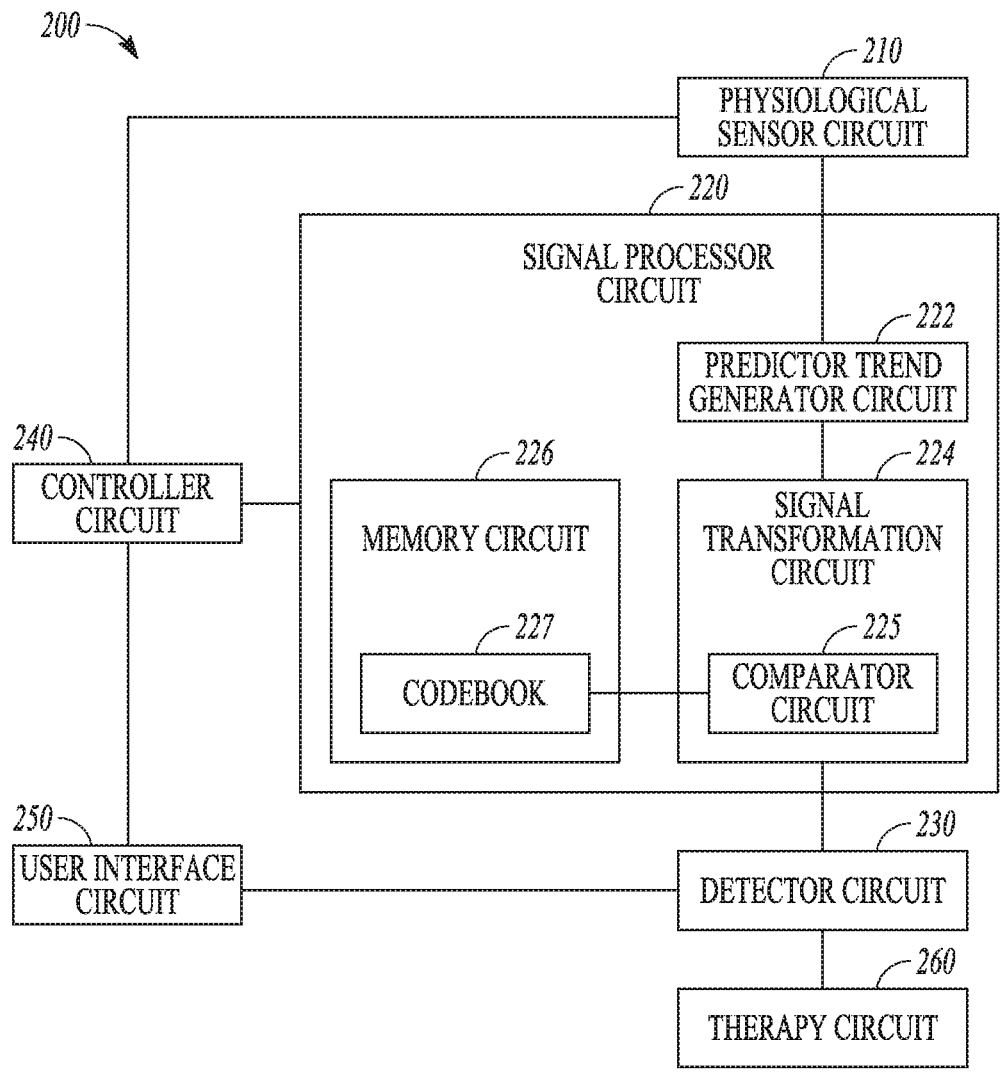
FIG. 2 illustrates generally an example of a target physiological event detection system configured to detect a target physiological event from a patient.

FIG. 2 illustrates generally an example of a target physiological event detection system 200 that may be configured to detect a target physiological event from a patient, such as a WHF event. The target physiological event detection system 200 may be an embodiment of the worsening cardiac condition detector 113. The target physiological event detection system 200 may include one or more of a physiological sensor circuit 210, a signal processor circuit 220, a detector circuit 230, a controller circuit 240, and a user interface unit 250.

The physiological sensor circuit 210 may include a sense amplifier circuit to sense a physiological signal sensed from a patient during a specified time period, such as a physiological signal containing information indicative of status or progression of HF. In an example, the sense amplifier circuit may be coupled to one or more electrodes such as the electrodes on one or more of the leads 108A-C or the can housing 112, one or more sensors, or one or more patient monitors, where the sensing circuit may sense at least one physiological signal from the patient. The physiological sensor circuit 210 may include one or more other sub-circuits to digitize, filter, or perform other signal conditioning operations on the received physiological signal. In another example, the physiological sensor circuit 210 may receive the one or more physiological signals from a storage device such as an electronic medical record (EMR) system, such as in response to a command signal provided by a system user, such as a clinician.

In an example, the physiological sensor circuit 210 may be coupled to one or more electrodes on one or more of the leads 108A-C or the can housing 112 to measure an impedance signal from a patient. The impedance may include a plurality of measurements of thoracic impedance or cardiac impedance. The impedance may be produced by injecting current between a first pair of electrodes and sensing the resultant voltage across a second pair of electrodes. For example, the impedance may be sensed across an RA electrode 141 or 142 and the can housing 112 ($Z_{RA-Can}$), across an RV electrode 152, 153 or 154 and a can housing 112 ($Z_{RV-Can}$), or across an LV electrode selected from electrodes 161-164 and the can housing 112 ($Z_{RV-Can}$). The impedance may include an impedance vector where the voltage sensing electrodes are the currently injection electrodes are orthogonal to each other, such as selected from RA, RV, or LV electrodes ($Z_{RA-RV-LV}$). In various examples, the physiological sensor circuit 210 may alternatively or additionally receive one or more of electrocardiograph (ECG) or electrograms (EGM) such as sensed from electrodes on one or more of the leads 108A-C or the can housing 112, a pulmonary artery pressure signal, an RV pressure signal, an LV coronary pressure signal, a coronary blood temperature signal, a blood oxygen saturation signal, a heart sound (HS) signal that includes one or more of heart sound components including first (S1), second (S2), third (S3), or fourth (S4) hear sounds, a respiration signal, or an activity signal, among others.

The signal processor circuit 220, coupled to the physiological sensor circuit 210, may generate from the sensed physiological signal a plurality of transformed indices for use in detecting a target physiological event such as a WHF event. In an example, the signal processor circuit 220 may be implemented as a part of a microprocessor circuit. The microprocessor circuit may be a dedicated processor such as a digital signal processor, application specific integrated circuit (ASIC), microprocessor, or other type of processor for processing information including the physiological signals received from the physiological sensor circuit 210. Alternatively, the microprocessor circuit may be a general purpose processor that may receive and execute a set of instructions of performing the functions, methods, or techniques described herein.

In an example such as illustrated in FIG. 2, the signal processor circuit 220 may include circuit sets comprising one or more other circuits or sub-circuits, that may, alone or in combination, perform the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

As illustrated in FIG. 2, the signal processor circuit 220 may include a circuit set including a predictor trend generator circuit 222, a signal transformation circuit 224, and a memory circuit 226. The predictor trend generator circuit 222 may include a filter circuit to filter the sensed physiological signal X(t) to produce a trend of a signal metric $X_m(t)$. In an example, the signal metric may include statistical parameters extracted from the sensed physiological signal, such as signal mean, median, or other central tendency measures or a histogram of the signal intensity, among others. In an example, the signal metric may include morphological parameters extracted from the sensed physiological signal, such as maximum or minimum within a specified time period such as a cardiac cycle, positive or negative slope or higher order statistics, signal power spectral density at a specified frequency range, among other morphological descriptors. Depending on the types of the sensed physiological signal, examples of the signal metrics may include thoracic impedance magnitude, S3 heart sound intensity, a ratio of S3 heart sound intensity to a reference heart sound intensity (such as S1 heart sound intensity, heart sound signal energy between R-wave and S2, or heart sound signal energy within a cardiac cycle), a respiration rate, a tidal volume, a ratio a respiration rate to a tidal volume, a minute ventilation, a posture, an activity intensity, or a time duration when the activity intensity is within a specified range or above a specified threshold, among others. In some examples, the signal metric may include composite signal metrics generated using two or more physiological signals, such as a systolic timing interval between an R-wave and a S1 heart sound within the same cardiac cycle, or between S1 heart sound and S2 heart sound within the same cardiac cycle.

The signal metric trend $X_m(t)$ may include multiple measurements of the signal metric during a specified period of time. In an example, the signal metric trend may include a daily trend including daily measurement of a signal metric over a specified number of days. The daily measurement may be determined as a central tendency of a plurality of measurements obtained within a day. In an example, a thoracic impedance trend may be generated using portions of the received impedance signal during identical phases of a cardiac cycle such as within a certain time window relative to R-wave in a ECG signal), or at identical phases of a respiratory cycle such as within an inspiration phase or an expiration phase of a respiration signal. This may minimize or attenuate the interferences such as due to cardiac or respiratory activities, in the impedance measurements. The thoracic impedance trend may be generated using impedance measurements collected during one or more impedance acquisition and analysis sessions. In an example, an impedance acquisition and analysis session may start between approximately 5 a.m. and 9 a.m. in the morning, and lasts for approximately 2-8 hours. In another example, the impedance acquisition and analysis session may be programmed to exclude certain time periods, such as night time, or when the patient is asleep. The impedance parameter may be determined as a median of multiple impedance measurements acquired during the impedance acquisition and analysis session.

The predictor trend generator circuit 222 may generate from signal metric trend $X_m(t)$ a predictor trend $X_p(t)$ that indicates a temporal change of the physiological signal. In an example, the predictor trend may be determined based on a comparison between short-term values and baseline values of the signal metric trend. A baseline value may include a statistical measure such as a central tendency of the measurements of the signal metric within a first time window ($W_L$). A short-term value may include a statistical measure such as a central tendency of the measurements of the signal metric within a second time window ($W_S$). In some examples, the second time window $W_S$ may have a shorter duration than the first time window $W_L$. In some examples, at least a portion of the first time window $W_L$ precedes the second time window $W_S$ in time, and the baseline value represents a historical reference value of the signal metric. The predictor trend may be determined as a relative difference between the short-term and baseline values. In some examples, the predictor trend may be determined using a linear or nonlinear combination of the relative differences between multiple short-term values corresponding to multiple first time windows and multiple baseline values corresponding to multiple second time windows, wherein the differences may be scaled by respective weight factors which may be based on timing information associated with corresponding multiple short-term window, such as described by Thakur et al., in U.S. Patent Application No. 62/236,416, entitled "PREDICTIONS OF WORSENING HEART FAILURE", which is herein incorporated by reference in its entirety.

The signal transformation circuit 224 may transform the predictor trend $X_p(t)$ into a plurality of transformed indices $Y(t)$ using a transformation operator $\Omega$, that is, $Y(t)=\Omega(X_p(t))$. The transformation operator $\Omega$ may be a mapping that preserves timing of the predictor trend $X_p(t)$, such that the transformed indices $Y(t)$ have the same data length as, and correspond in time with, the predictor trend $X_p(t)$. In an example, the transformation $\Omega$ may include an isometric transformation that preserves relative intensity of the predictor trend $X_p(t)$. In an example, the transformation $\Omega$ is based on a plurality of thresholds. The thresholds may include a plurality of threshold pairs $\{(TO_i, TR_i)\}$ for i=1, 2 ... N, where $TO_i$ denotes an onset threshold, $TR_i$ denotes a reset threshold, and N denotes the number of threshold pairs. The signal transformation circuit 224 may include a comparator circuit 225 that compares an intensity (such as an amplitude) of the $X_p(t)$ to the TO and TR to identify a first threshold crossing when the $X_p(t)$ exceeds the TO and a subsequent second threshold crossing when the $X_p(t)$ subsequently falls below the TR. The signal transformation circuit 224 may then assign a specified code C(t) for the portion of the $X_p(t)$ between the first and subsequent second threshold crossings.

In an example as illustrated in FIG. 2, the signal transformation circuit 224 may be coupled to the memory circuit 226, and transform the predictor trend $X_p(t)$ using a codebook 227 stored in the memory circuit 226. The codebook 227 may include an association between the plurality of threshold pairs $\{(TO_i, TR_i)\}$ and corresponding code words $\{C_i\}$. In an example, the threshold pairs $\{(TO_i, TR_i)\}$ may be mapped to the code words $\{C_i\}$, such that the codebook 227 has the same length N (i.e., the number of code words) as the number of the threshold pairs stored in the codebook 227.

The code words $\{C_i\}$ may include numerical codes within a specified range. A threshold pair with a higher onset threshold or a higher reset threshold may be associated with a larger numerical code than a threshold pair with a lower onset threshold or a lower reset threshold. In some examples, a threshold pair with a lower onset threshold or a lower reset threshold may be associated with a larger numerical code than a threshold pair with a higher onset threshold or a higher reset threshold. By way of non-limiting example, Table 1 shows a codebook with numerical codes between 1 and 20. For two threshold pairs $(TO_i, TR_i)$ and $(TO_j, TR_j)$, if the thresholds are related by $TO_i \geq TO_j$ or $TR_i \geq TR_j$, then the numerical codes are related by $C_i \geq C_j$. In some examples, the two threshold values within each threshold pair may be equal (i.e. $TO_i=TR_i$).

TABLE 1

An example of a codebook based on threshold pairs.

| Threshold Pairs | Code words (C) |
|---|---|
| (TO, TR) | |
| $(TO_{20}, TR_{20})$ | 20 |
| $(TO_{19}, TR_{19})$ | 19 |
| ... | ... |
| $(TO_2, TR_2)$ | 2 |
| $(TO_1, TR_1)$ | 1 |

To transform the predictor trend $X_p(t)$ using a codebook 227, the signal transformation circuit 224 may identify from the codebook 227 a relevant threshold pair $(TO_i, TR_i)$ for a specified portion of the predictor trend $X_p(t)$. The specified portion of the $X_p(t)$ temporally occurs after the first threshold crossing where the $X_p(t)$ exceeds the $TO_i$, and prior to the second threshold crossing where the $X_p(t)$ subsequently falls below the $TR_i$. The signal transformation circuit 224 may assign to the specified portion of the $X_p(t)$ a numerical code C(i) associated with the identified relevant threshold pair $(TO_i, TR_i)$, according to the codebook 227. In an example, the same numerical code C(i) may be assigned to all data samples of the specified portion of the $X_p(t)$. The signal transformation circuit 224 may similarly process the entirety of the predictor trend $X_p(t)$ to generate the transformed indices Y(t), which may have the same data length and preserved timings as the predictor trend $X_p(t)$. Examples of the signal metric trend $X_m(t)$ extracted from a physiological signal and the corresponding predictor trend $X_p(t)$ and the transformed indices Y(t) are discussed below, such as with respect to FIG. 8.

In an example, the signal transformation circuit 224 may identify from the codebook 227 two or more relevant threshold pairs for a specified portion of the predictor trend $X_p(t)$, such as at least threshold pairs $(TO_i, TR_i)$ and $(TO_j, TR_j)$. The signal transformation circuit 224 may determine between the two or more relevant threshold pairs a dominant threshold pair that has a larger onset threshold or a larger reset threshold than any other of the identified relevant threshold pairs, and assign to the specified portion of the first predictor trend a numerical code associated with the dominant threshold pair. For example, if only two relevant threshold pairs $(TO_i, TR_i)$ and $(TO_j, TR_j)$ are identified, and if $TO_i \geq TO_j$ and $TR_i \geq TR_j$, then the threshold pair $(TO_i, TR_i)$ is dominant, and the numerical code C(i) associated with the dominant threshold pair is assigned to the specified portion of the $X_p(t)$. Examples of determining relevant or dominant threshold pair from the codebook and transforming the predictor trend $X_p(t)$ are discussed below, such as with respect to FIGS. 3A-B.

The detector circuit 230 may be coupled to the signal processor circuit 220, and configured to use the transformed indices detect a target physiological event or condition, such as a physiological event indicative of an onset of a disease, worsening of a disease state, or a change of a disease state. In an example, the detector circuit 230 may detect the presence of an event indicative of worsening cardiac condition such as a WHF event, pulmonary edema, pneumonia, chronic obstructive pulmonary disease (COPD), myocardial infarction, acute renal disease, among others. In some examples, the detector circuit 230 may include a comparator circuit to compare the transformed indices Y(t) to a specified threshold, and generate an indication of detection of the target physiological event if the Y(t) exceed the specified threshold.

In some examples, the target physiological event detection system 200 may detect the target physiological event using two or more signal metric trends and respective codebooks created for the signal metrics and stored in the memory circuit 226. The predictor trend generator circuit 222 may generate a first signal metric trend $X1_m(t)$ using a first physiological signal, and generate a second signal metric trend $X2_m(t)$ different from $X1_m(t)$ using the first physiological signal or a different second physiological signal such as sensed by the physiological sensor circuit 210. The predictor trend generator circuit 222 may generate first and second predictor trends ($X1_p(t)$ and $X2_p(t)$, respectively) using the respective first and second signal metric trends. The signal transformation circuit 224 may use a first codebook to transform the first predictor trend $X1_p(t)$ into a first plurality of transformed indices Y1(t), and use a second codebook to transform the second predictor trend $X2_p(t)$ into a second plurality of transformed indices Y2(t). In an example, the threshold pairs in the first codebook may differ from the plurality of threshold pairs in the second codebook, while the first and second codebooks may have the same code words such as numerical codes within a specified value range such as between 1 and 20. As such, even if the first and second signal metric trends may have different characteristics such as data range, through transformation as performed by the signal transformation circuit 224, the corresponding transformed indices Y1(t) and Y2(t) are within the same data range (such as between 1 and 20) and therefore may be easily comparable. The detector circuit 230 may detect the target physiological event using both the first and second plurality of transformed indices Y1(t) and Y2(t), such as a linear or a nonlinear combination of Y1(t) and Y(2).

In an example, the target physiological event detection system 200 may detect the target physiological event using a joint transformation $\Omega'$ of two or more predictor trends, such as including the $X1_p(t)$ and $X2_p(t)$. The two or more predictor trends may be jointly transformed into transformed indices: $Y(t)=\Omega'(X1_p(t), X2_p(t))$. In an example, the joint transformation $\Omega'$ is based on a codebook that may include an association between a plurality of multi-dimensional thresholds and corresponding code words such as numerical codes $\{C_i\}$ within a specified range. In an example, the multi-dimensional thresholds such as $\{(TO1_i, TR1_i; TO2_i, TR2_i)\}$ may include a first threshold pair $(TO1_i, TR1_i)$ for the first predictor trend $X1_p(t)$ and a second threshold pair $(TO2_i, TR2_i)$ for the second predictor trend $X2_p(t)$. The signal transformation circuit 224 may compare a portion of the $X1_p(t)$ during a specified time segment and a portion of the $X2_p(t)$ during the same specified time segment to the multi-dimensional threshold pairs in the codebook. If during the specified time segment, the portion of the first predictor trend $X1_p(t)$ falls between the threshold crossings associated with $(TO1_i, TR1_i)$, and the portion of the second predictor trend $X2_p(t)$ falls between the threshold crossings associated with $(TO2_i, TR2_i)$, then the signal transformation circuit 224 may determine the value of the transformed indices Y(t) during the specified time segment as the numerical code $C_i$. The signal transformation circuit 224 may similarly process the entirety of the predictor trends $X1_p(t)$ and $X2_p(t)$ to generate the transformed indices Y(t).

The controller circuit 240 may control the operations of the physiological sensor circuit 210, the signal processor circuit 220, the detector circuit 230, and the data and instruction flow between these components. The user interface unit 250 may be configured to present programming options to the user and receive user's programming input. The user interface unit 250 may include an input device, such as a keyboard, on-screen keyboard, mouse, trackball, touchpad, touch-screen, or other pointing or navigating devices. The input device may enable a system user to program the parameters used for sensing the physiological signals. The user interface may include an output unit that may generate a presentation of information including the detected cardiac condition. The information may be presented in a table, a chart, a diagram, or any other types of textual, tabular, or graphical presentation formats, for displaying to a system user. The presentation of the output information may include audio or other human-perceptible media format to alert the system user of the detected progression of cardiac condition, such as when the plurality of transformed indices satisfies a detection criterion. In an example, at least a portion of the user interface unit 250, such as the user interface, may be implemented in the external system 120.

In some examples, the target physiological event detection system 200 may additionally include a therapy circuit 260 that is configured to deliver a therapy to the patient in response to the detection of the target physiological event or condition. Examples of the therapy may include electrostimulation therapy delivered to the heart, a nerve tissue, other target tissues in response to the detection of the target physiological event, or drug therapy including delivering drug to a tissue or organ. In some examples, the therapy circuit 260 may be used to modify an existing therapy, such as adjusting a stimulation parameter or drug dosage.

Figures 3A, 3B:
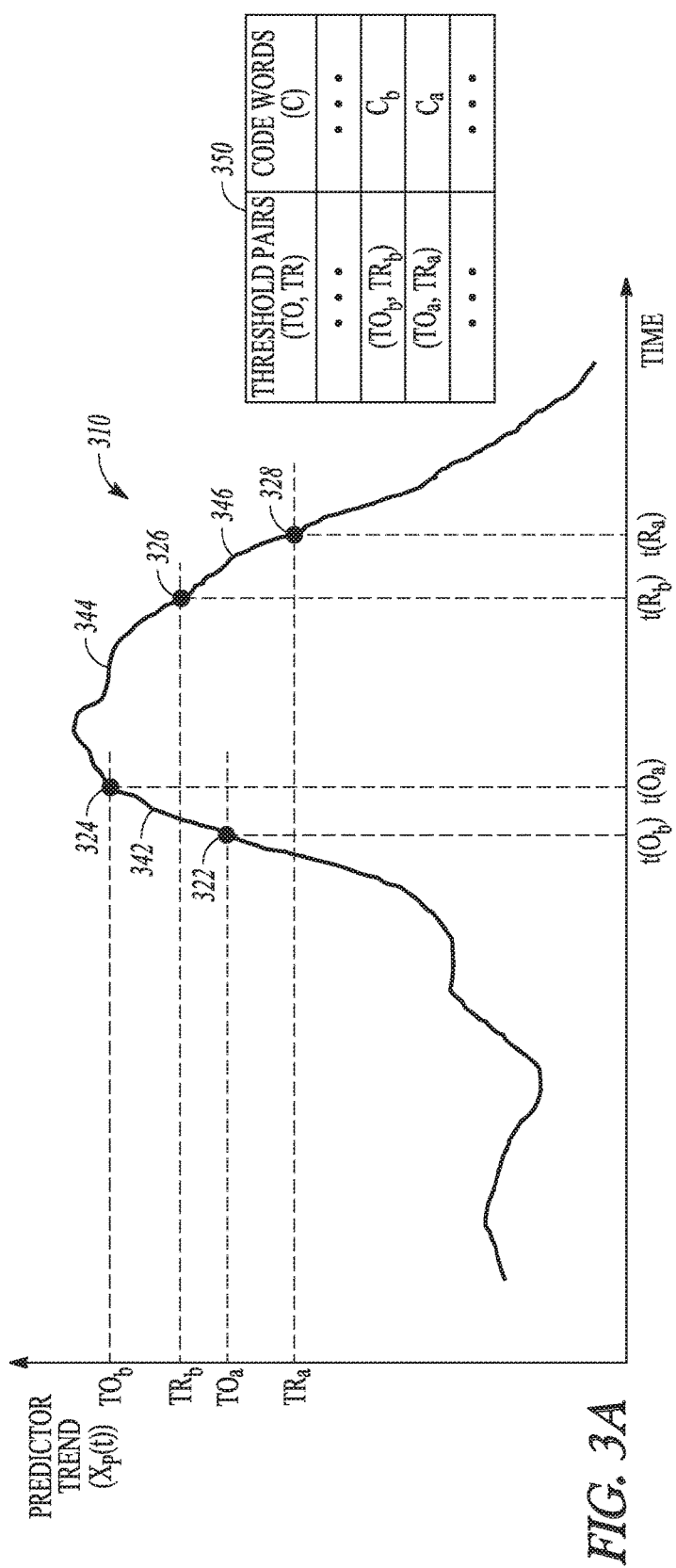
FIGS. 3A-B illustrate generally an example of signal transformation using a codebook.

FIGS. 3A-B illustrate generally an example of signal transformation using a codebook 350. Relevant or dominant threshold pairs may be determined from the codebook 350 and used to transform the predictor trend 310 into a sequence of transformed indices. The codebook 350, which may be an embodiment of the codebook 227 stored in the memory circuit 226, includes a plurality of threshold pairs including $(TO_a, TR_a)$ and $(TO_b, TR_b)$, where $TO_b > TO_a$ and $TR_b > TR_a$. The signal transformation circuit 224 may compare the predictor trend 310 to the plurality of threshold pairs in the codebook 350, and determine the threshold crossings 322, 324, 326 and 328. The threshold crossing 322 occurs when the predictor trend 310 exceeds the threshold $TO_a$ at $t(O_a)$, the threshold crossing 324 occurs when the predictor trend 310 exceeds the threshold $TO_b$ at $t(O_b)$, the threshold crossing 326 occurs when the predictor trend 310 falls below the threshold $TR_b$ at $t(R_b)$, and the threshold crossing 328 occurs when the predictor trend 310 falls below the threshold $TR_3$ at $t(R_a)$. The identified threshold crossings 322, 324, 326 and 328 define consecutive portions of the predictor trend 310 between $t(O_a)$ and $t(R_a)$, including a first predictor trend portion 342 between the threshold crossings 322 and 324, a second predictor trend portion 344 between the threshold crossings 324 and 326, and a third predictor trend portion 346 between the threshold crossings 326 and 328. Both the predictor trend portions 342 and 346 temporally occur between the threshold crossings 322 and 328, which are associated with the threshold pair $(TO_a, TR_a)$; therefore, the threshold pair $(TO_a, TR_a)$ is a relevant threshold pair. The signal transformation circuit 224 may transform the predictor trend portions 342 and 346 each into respective portions 362 and 366 of the transformed indices 360 in FIG. 3B, where both portions 362 and 366 have value of $C_a$ according to the codebook 350. The predictor trend portion 344 temporally occurs between the threshold crossings 322 and 328 which is associated with the threshold pair $(TO_a, TR_a)$, and also occurs between the threshold crossings 324 and 326 which is associated with the threshold pair $(TO_b, TR_b)$. Therefore, both the threshold pairs $(TO_a, TR_a)$ and $(TO_b, TR_b)$ are relevant threshold pairs. Because $TO_b > TO_a$ and $TR_b > TR_3$, the signal transformation circuit 224 may determine $(TO_b, TR_b)$ as the dominant threshold pairs, and transform the predictor trend portion 344 into the corresponding portion 364 of the transformed indices 360. The portion 364 has a value of $C_b$, according to the codebook 350. The signal transformation circuit 224 may similarly process the entirety of the predictor trend 310 to generate the transformed indices 360.

Figure 4:
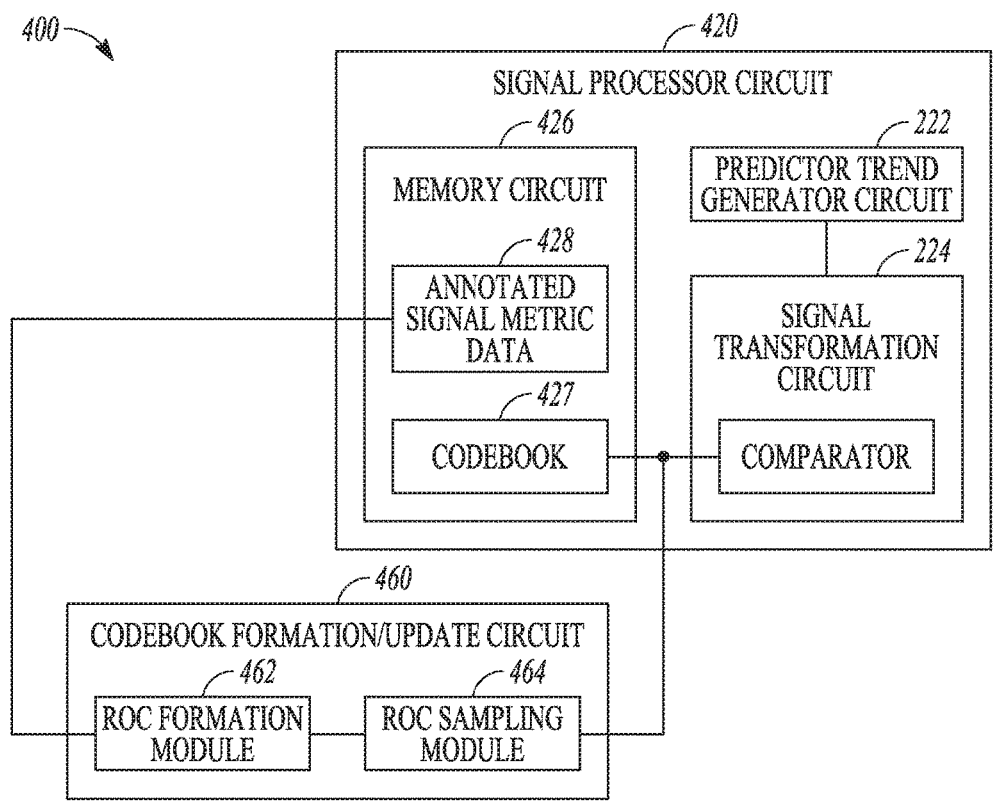
FIG. 4 illustrates generally an example of a portion of a target physiological event detection system with a codebook formation/update circuit.

FIG. 4 illustrates generally an example of a portion of a target physiological event detection system 400 including a codebook formation/update circuit 460. The target physiological event detection system 400, which may be an embodiment of the system 200, may include a signal processor circuit 420 that may be an embodiment of the signal processor circuit 220 as illustrated in FIG. 2. Compared to the system 200, the target physiological event detection system 400 may further include the codebook formation/update circuit 460 to generate a codebook 427 for storing in the memory circuit 426, or to update an existing codebook 427 that has already been stored in the memory circuit 426. The codebook formation/update circuit 460 may include hardware, software, or firmware communicatively coupled to one or more processors in order to carry out the operations described herein. In an example, the codebook formation/update circuit 460 may be implemented as a part of a microprocessor circuit. Portions of the codebook formation/update circuit 460 may be implemented in the IMD 110, in the external system 120, or distributed between the IMD 110 and the external system 120. In an example, portions of the codebook formation/update circuit 460 may be implemented as a part of the signal processor circuit 420.

In an example, the codebook formation/update circuit 460 may generate or update the codebook using a receiver operating characteristic (ROC) of a specified signal metric. The codebook formation/update circuit 460 may include a ROC formation module 462 and a ROC sampling module 464. The ROC formation module 462 may be coupled to the memory circuit 426 to receive annotated signal metric data 428 stored in the memory circuit 426. The annotated signal metric data may include both signal trends pertaining to a specified signal metric collected from a selected cohort of patients (such as CHF patients with risks of developing WHF events) as well as annotations of the signal metric trends, which may include known information about the target physiological event, such as clinical diagnosis or decisions of presence or absence of the WHF event. The ROC may comprise a plurality of operating points indicating sensitivity statistics and false positive rate (FPR) statistics associated with a plurality of candidate threshold pairs, and may thus be used to describe a performance of a detector or a detection algorithm. The sensitivity statistic corresponding to a candidate threshold pair may be expressed in a percentage between 0 and 100% indicating a percentage of positive target events (such as annotated WHF events) that have correctly been detected by the detector or detection algorithm when operating with the candidate threshold pair. The FPR statistic corresponding to a candidate threshold pair may be expressed in a numerical value indicating a rate of incorrect detection of non-target event (such as annotated absence of WHF events) as a target event, per patient within a specified timeframe. In some examples, the ROC formation module 462 may receive the ROC that has been created and stored in the memory circuit 426, or receive it from the user interface unit 250.

The ROC sampling module 464 may partition the ROC into a plurality of ROC segments defined by boundary operating points associated with respective boundary threshold pairs. Each ROC segment is associated with a sensitivity statistics range, a FPR statistics range, and a range of onset and reset thresholds. The ROC sampling module 464 may assign respective code words for the partitioned ROC segments, and generate or update the codebook 427 including establishing an association between the boundary threshold pairs and the code words. The signal transformation circuit 224 may use the generated or updated codebook 427 to transform the predictor trend $X_p(t)$ to the transformed indices Y(t). Examples of the ROC and the sampling of ROC to generate or update the codebook are discussed below, such as with reference to FIGS. 5A-C.

Figure 5A:
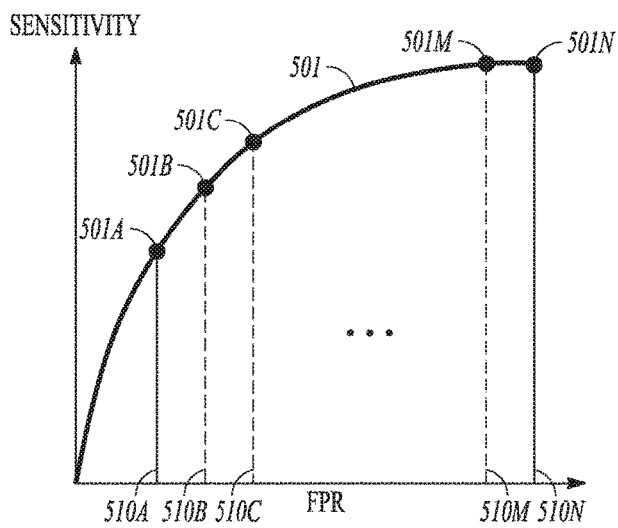
FIGS. 5A-C illustrate generally examples of receiver operating characteristic (ROC) sampling and the codebook formation or update using the sampled ROC.
Figure 5B:
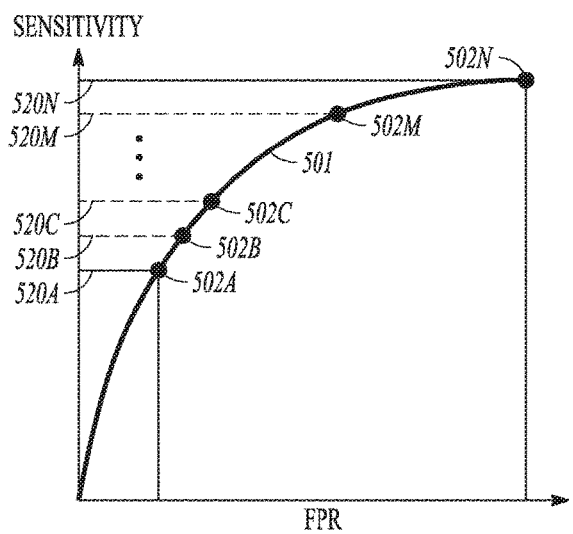
Figure 5C:
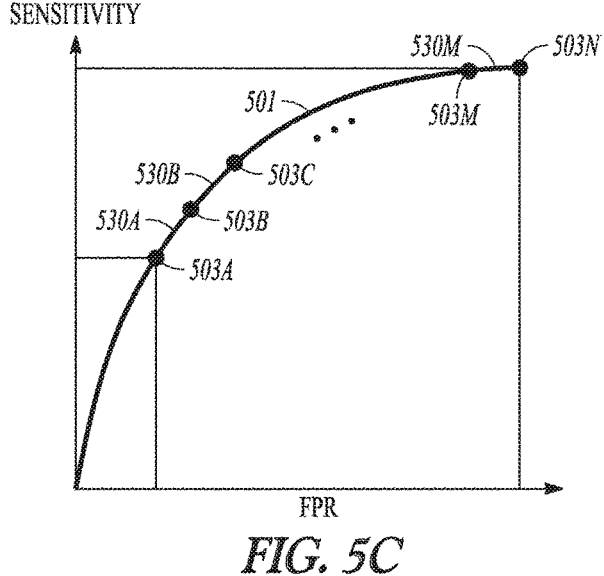

FIGS. 5A-C illustrate generally examples of ROC sampling and the codebook formation or update based on the sampled ROC. The ROC sampling may be based on sampling the FPR statistics, the sensitivity statistics, or an ROC curve that connects the plurality of operating points in a two-dimensional ROC plane spanned by the sensitivity statistics in the y-axis and the FPR statistics in the x-axis. In FIG. 5A, the FPR statistics of an ROC curve 501 are sampled within a specified FPR range such as between FPR(1) at 510A and FPR(2) at 510N. In an example, FPR(1) may be approximately 0 or approximately 1. In an example, FPR(2) may be approximately 4 or approximately 5. The sampling of FPR may be performed at specified sampling intervals such as to produce a plurality of intermediate FPRs 510B-M between the FPR(1) and FPR(2). In an example, the FPR may be linearly sampled at a sampling interval $\Delta_{FPR}$, such that the FPRs 510A-N are uniformly distributed with inter-FPR distance of $\Delta_{FPR}$. The FPRs 510A-N may correspond to the boundary operating points 501A-N on the ROC curve 501, which are associated with respective boundary threshold pairs. Respective code words may be assigned for the ROC segments defined by the boundary operating points 501A-N. A codebook may be generated by establishing an association between the boundary threshold pairs for the boundary operating points 501A-N and the code words, such as the codebook illustrated in Table 1.

FIG. 5B illustrates sampling of the sensitivity statistics (SENS) of the ROC curve 501 within a specified sensitivity range such as between SENS(1) at 520A and SENS(2) at 520N. In an example, SENS(1) may be approximately 0, or approximately 50%, or approximately 60%. In an example, SENS(2) may be approximately 100% or approximately 99%. Similar to the sampling of FPR, the sampling of the sensitivity statistics may be performed at specified sampling intervals such as to produce a plurality of intermediate sensitivities 520B-M between the SENS(1) and SENS(2). In an example, the sensitivity statistics may be linearly sampled at a sampling interval $\Delta_{SENS}$, such that the sensitivities 520A-N are uniformly distributed with inter-sensitivity distance of $\Delta_{SENS}$. The boundary operating points 502A-N corresponding to the sampled sensitivities 520A-N may be associated with respective boundary threshold pairs. Respective code words may be assigned for the ROC segments defined by the boundary operating points 502A-N, and a codebook may be generated by establishing an association between the boundary threshold pairs for the boundary operating points 502A-N and the code words, such as the codebook illustrated in Table 1.

FIG. 5C illustrates sampling a portion of the ROC curve including a specified portion of the operation points within a specified sensitivity range and a specified FPR range. In an example, the ROC curve portion is defined within the sensitivity range of approximately 50-80% and the FPR range of approximately 0.5-4. From the ROC curve 501, a boundary operating point 503A that corresponds to the lower bounds of the sensitivity and FPR (such as sensitivity of 500% and FPR of 0.5) within the respectively specified ranges, and a boundary operating point 503N that corresponds to the upper bounds of the sensitivity and FPR (such as sensitivity of 80% and FPR of 4) within the respectively specified ranges, may be identified. In an example, for the operating points between 503A and 503N, the sensitivity and FPR statistics may be expressed as fractions of the upper bounds of the sensitivity and the FPR. The ROC curve portion between the operating points 503A and 503N may be sampled at specified sampling intervals such as to produce a plurality of intermediate boundary operating points 503B-M. In an example, the sampling may be performed such that the boundary operating points 503B-M are equally spaced along the ROC curve 501 according to a distance measure. In an example, the boundary operating points 503B-M are determined such that the Euclidean distances 530A-M between adjacent operating points of 503A-N on the two-dimensional ROC plane are all equal. Respective code words may be assigned for the ROC segments defined by the boundary operating points 503A-N, and a codebook may be generated by establishing an association between the boundary threshold pairs for the boundary operating points 503A-N and the code words, such as the codebook illustrated in Table 1.

In an example, the code words are numerical codes, and a boundary threshold pair associated with an operating point with a lower sensitivity or a lower FPR may be mapped to a higher numerical code. For example, the boundary threshold pair ($TO_A$, $TR_A$) associated with the operating point 501A (or 502A or 503A) may be mapped to a higher numerical code than the boundary threshold pair ($TO_B$, $TR_B$) associated with the operating point 501B (or 502B or 503B). In an example, the FPR statistics may be sampled to generate 20 boundary operating points (i.e., N=20). The codebook may be generated such that the boundary threshold pair associated with the operating point 501A (or 502A or 503A) is mapped to a numerical code of 20, and the boundary threshold pair associated with 501B-N (or 502B-N or 503B-N) are respectively mapped to numerical codes of 19 down to 1.

Figure 6:
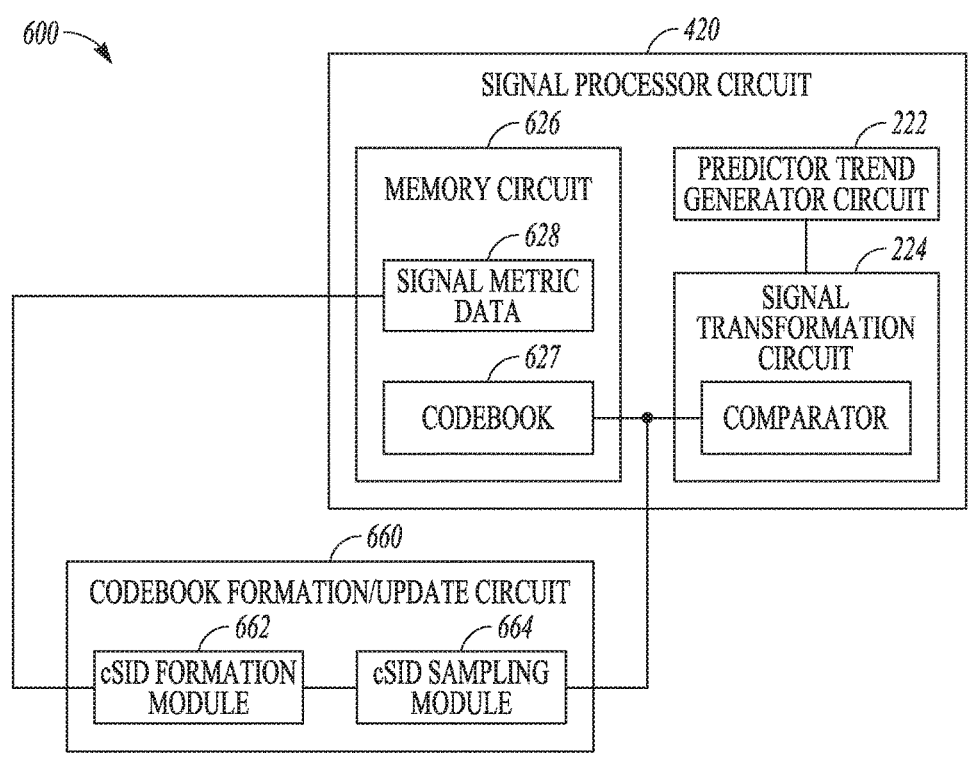
FIG. 6 illustrates generally an example of a portion of a target physiological event detection system including a codebook formation/update circuit.

FIG. 6 illustrates generally an example of a portion of a target physiological event detection system 600 including a codebook formation/update circuit 660. The target physiological event detection system 600, which may be an embodiment of the system 200, may comprise a signal processor circuit 620 that may be an embodiment of the signal processor circuit 220, and a codebook formation/update circuit 660 to generate a codebook 627 for storing in the memory circuit 626, or to update an existing codebook 627 that has been stored in the memory circuit 626. Similar to the codebook formation/update circuit 460, the codebook formation/update circuit 660 may be implemented as a part of a microprocessor circuit, or include hardware, software, or firmware communicatively coupled to one or more processors in order to carry out the operations described herein. Portions of the codebook formation/update circuit 460 may be implemented in the IMD 110, in the external system 120, or distributed between the IMD 110 and the external system 120.

The codebook formation/update circuit 660 may include a composite signal intensity distribution (cSID) formation module 662 and a cSID sampling module 664. The cSID formation module 662 may be coupled to the memory circuit 626 to receive signal metric data 628, including a plurality of predictor trends pertaining to a specified signal metric, collected from a selected cohort of patients such as CHF patients with risks of developing WHF events. Unlike the annotated signal metric data 428 in FIG. 4, annotations of the signal metric trends such as clinical decisions of presence or absence of the WHF event may not be required to form the codebook by the codebook formation/update circuit 660. The cSID formation module 662 may generate the cSID that represents a statistical distribution of the magnitude of the plurality of the prediction trends. In an example, the statistical distribution may include a histogram that includes percentile frequencies of the magnitude of the predictor trends across a number of magnitude bins. Each magnitude bin may be defined by boundary candidate onset and reset thresholds. In an example, the statistical distribution may include a continuous distribution such as by interpolating, extrapolating, or smoothing of the histogram.

The cSID sampling module 664 may partition the cSID into a plurality of distribution segments defined by percentile frequency thresholds (PFTs) associated with respective boundary onset or reset thresholds. The cSID sampling module 664 may assign respective code words for the partitioned distribution segments, and generate or update the codebook 627 including establishing an association between the boundary onset or reset thresholds and the code words. By way of non-limiting example, Table 2 illustrates a codebook 627 that maps the boundary onset thresholds to the corresponding numeral codes 1 to 20. The codebook 627 may alternatively include an association between the PFTs and the code words, such as illustrated in Table 3. For example, if $PFT_i > PFT_j$, then the corresponding code words are related by $C_i > C_j$. In some examples, the codebook formation/update circuit 660 may generate the boundary reset thresholds as a linear or nonlinear function ($f$) of the boundary onset thresholds, that is, $TR_i = f(TO_i)$. In an example, $TR = \alpha \cdot TO$, where $\alpha$ is a scaling factor $0 < \alpha < 1$ such that the reset threshold $TR_i$ is less than the corresponding onset threshold $TO_i$. The codebook may include an association between the boundary threshold pairs $((TO_i, TR_i))$ and the corresponding code words. Examples of the cSID and the sampling of cSID to generate or update the codebook are discussed below, such as with reference to FIGS. 7A-B.

TABLE 2

An example of a codebook based on boundary percentile frequencies (PF).

| Onset Threshold | Code word |
|---|---|
| TO (PFT$_{20}$) | 20 |
| TO (PFT$_{19}$) | 19 |
| ... | ... |
| TO (PFT$_2$) | 2 |
| TO (PFT$_1$) | 1 |

TABLE 3

An example of a codebook based on boundary percentile frequencies.

| Thresholds (PFT, %) | Code word |
|---|---|
| PFT$_{20}$ | 20 |
| PFT$_{19}$ | 19 |
| ... | ... |
| PFT$_2$ | 2 |
| PFT$_1$ | 1 |

The signal transformation circuit 224 may use the generated or updated codebook 627 to transform the predictor trend $X_p(t)$ to the transformed indices $Y(t)$. In an example, the signal transformation circuit 224 may be configured to produce a signal intensity distribution (SID) of the predictor trend $X_p(t)$, and to transform the SID of $X_p(t)$ using the codebook 627. A portion of the predictor trend $X_p(t)$ having a SID between $PF_i$ and $PF_{i+1}$ may be transformed to indices with a value of $C_i$, or a numerical value of $C_i = i$, such as according to the codebook shown in Table 3.

Figure 7A:
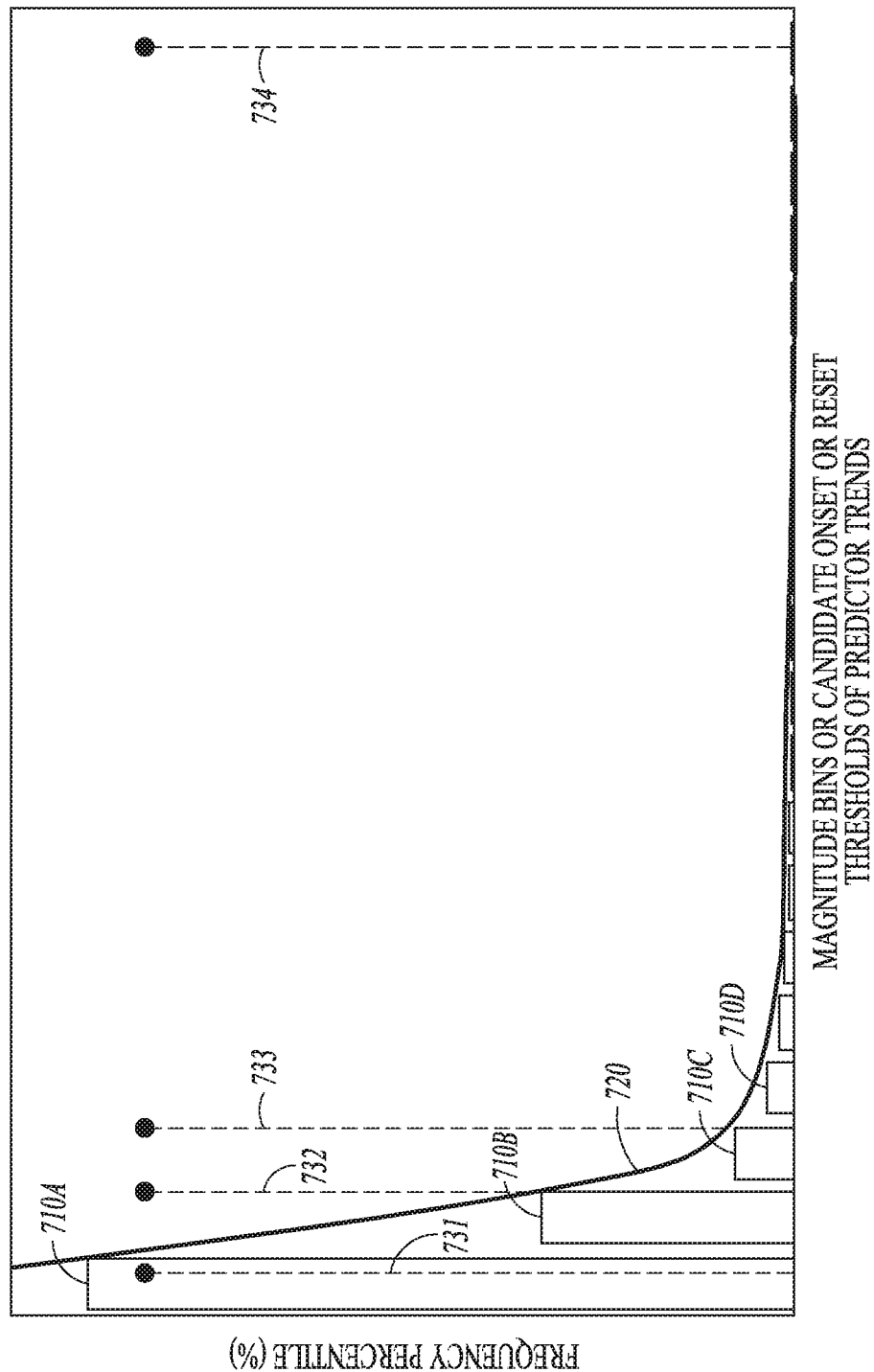
FIG. 7A-B illustrate generally examples of a composite signal intensity distribution (cSID) and codebook formation based on sampling of the cSID.
Figure 7B:
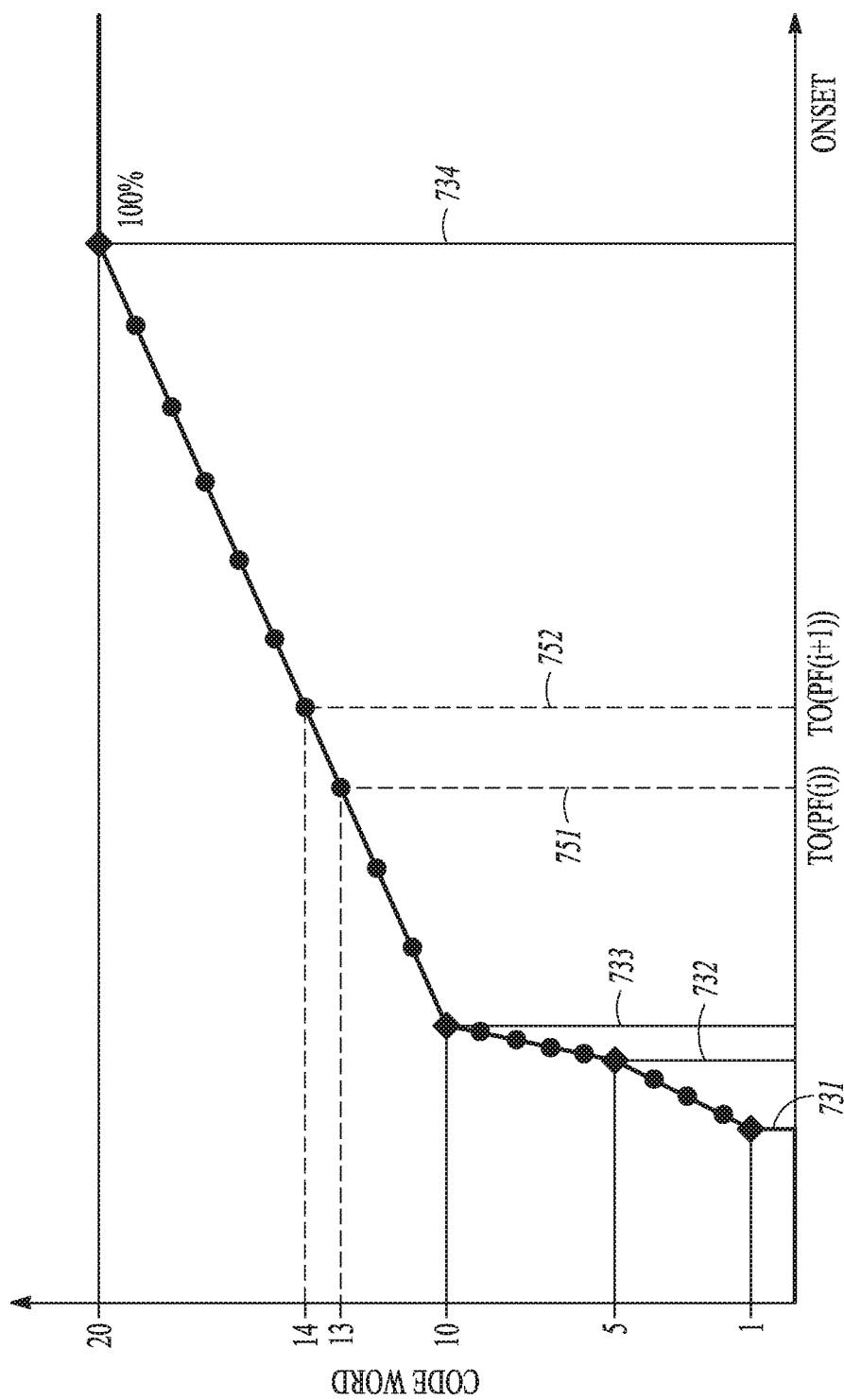

FIGS. 7A-B illustrate generally examples of a composite signal intensity distribution (cSID) and codebook formation based on sampling of the cSID. As illustrated in FIG. 7A, the cSID, which may be formed by the cSID formation module 662, may include a histogram of the magnitude of the predictor trends across a number of magnitude bins including 710A-D, among other magnitude bins. Each magnitude bin defines a range of candidate onset or reset threshold of the magnitude of the predictor trends. Generally, a predictor trend $X_p(t)$ may spend more time at a lower magnitude range (such as a baseline of $X_p(t)$) than at a higher magnitude range (such as a peak of $X_p(t)$), a higher percentile frequency may be found for a lower bin, and the percentile frequency decreases as magnitude bins increases. The histogram may be interpolated, extrapolated, or smoothened to produce a continuous distribution function 720.

The cSID sampling module 664 may sample the histogram, or the continuous distribution function 720, including sampling the candidate onset or reset thresholds (i.e., the x-axis of FIG. 7A) within a specified threshold range to produce boundary onset or reset thresholds, such as within the upper half of the entire range of the onset or reset thresholds, or within the top quarter of the entire range of the onset or reset thresholds. The candidate onset or reset thresholds may be sampled at specified sampling intervals, such as a linearly sampling where the resulting boundary thresholds are uniformly distributed within the specified threshold range. A codebook may be generated by establishing an association between the boundary onset or reset thresholds and the code words.

The sampling of the histogram or the continuous distribution function 720 may alternatively include sampling the percentile frequencies (i.e., the y-axis of FIG. 7A) within a specified percentile frequency range to produce boundary percentile frequencies, such as between approximately 50% and 100%, or between approximately 60% and 100%. The percentile frequencies may be sampled at specified sampling intervals, such as a linearly sampling where the resulting boundary percentile frequencies are uniformly distributed within the specified frequency range. A codebook may be generated by establishing an association between the boundary percentile frequencies and the code words. Additionally or alternatively, boundary onset or reset thresholds corresponding to the boundary percentile frequencies may be determined according to the histogram or the continuous distribution function 720, and the codebook may include an association between the boundary onset or reset thresholds and the code words.

In an example, in lieu of the linear sampling of the percentile frequency range or the onset or resent threshold range, the cSID sampling module 664 may partition the specified percentile frequency range or the onset or resent threshold range into two or more pieces, and perform a piece-wise linear sampling within the two or more pieces. The cSID sampling module 664 may receive from the memory circuit 626 or the user interface unit 250 one or more anchor percentile frequencies (APF), and partition the specified percentile frequency range using the APFs. Each APF corresponds to an onset or reset threshold, where the APF represents the percentage of signal magnitude of the predictor trends that falls below the corresponding onset or reset threshold. In a non-limiting example, the APFs may include 60%, 90%, 95%, and 100%, with the corresponding boundary onset thresholds 731-734 denoted by TO(60%), TO(90%), TO(95%), and TO(100%) which may be determined using the histogram or the continuous distribution function 720. In an example, for APF=60%, the corresponding onset threshold TO(60%) may be determined such that an integral of the distribution function 720 up to the threshold TO(FPR(i)), or an accumulation of the percentile frequencies of the histogram (as shown in FIG. 7A) across magnitude bins up to TO(FPR(i)), equals 60%. The boundary onset threshold TO(60%) thus determined indicates that 60% of the signal magnitude of the predictor trends falls below TO(60%). A higher APF may have a higher corresponding onset or reset threshold. For example, TO(100%) at 734 is greater than any other thresholds 731-733, and indicates all (100%/o) magnitude of the predictor trends is below the threshold TO(100%). As illustrated in FIG. 7A, the APFs partition the percentile frequency range into following pieces: <60%, 60-90%, 90-95%, and 95-100%. Correspondingly, the thresholds 731-734 partition the onset or reset threshold range (the x-axis of FIG. 7) into the following segments: <TO(60%)(i.e., below 731), TO(60%)-TO (90%) (i.e., between 731-732), TO(90%)-TO(95%) (i.e., between 732-733), and TO(95%)-TO(100%) (i.e., between 733-734).

FIG. 7B illustrates the piece-wise sampling of the onset or reset threshold within each of the segments defined by the thresholds 731-734 corresponding to the APFs. Each of the boundary onset thresholds TO(60%), TO(90%), TO(95%), and TO(100%) may be assigned a corresponding user-specified code word. In a non-limiting example, the thresholds TO(60%), TO(90%), TO(95%), and TO(100%) are respectively assigned numerical codes of 1, 5, 10 and 20. The cSID sampling module 664 may sample between two adjacent boundary onset thresholds TO($APF_1$) (with a corresponding numerical code of C($APF_1$)) and TO($APF_2$) (with a corresponding numerical code of C($APF_2$)) at a specified sampling interval to generate intermediate boundary onset thresholds. In an example, the cSID sampling module 664 may linearly sample the segment between TO($APF_1$) and TO($APF_2$) at a sampling interval, such that all codes between C($APF_1$) and C($APF_2$) are evenly distributed. The sampling interval may be determined as [TO($APF_2$)–TO($APF_1$)]/[C($APF_2$) and C($APF_1$)]. As illustrated in FIG. 7B, the piece-wise linear sampling within the segments defined by the thresholds 731-734 result in numerical codes 1-5 assigned for uniformly spaced boundary onset thresholds between TO(60%) and TO(90%), numerical codes 6-10 for uniformly spaced boundary onset thresholds between (90%) and TO(95%), and numerical codes 11-20 for uniformly spaced boundary onset thresholds between TO(95%) and TO(100%). For example, the boundary onset threshold TO($PF_i$) at 751, which corresponds to the boundary percentile frequency $PF_i$, has a numerical code of 13. The boundary onset threshold TO($PF_{i+1}$), which corresponds to the boundary percentile frequency $PF_{i+1}$, has a numerical code of 14. A codebook may be generated, which establishes an association between the boundary onset thresholds and the code words, such as the codebook shown in Table 2. The codebook may alternatively include an association between the percentile frequencies (which correspond to the boundary onset thresholds) and the code words, such as the codebook shown in Table 3. The signal transformation circuit 224 may transform a predictor trend $X_p(t)$ using the codebook. For example, a portion of $X_p(t)$ that falls between the onset thresholds TO($PF_i$) and TO($PF_{i+1}$) may be mapped to numerical code 13. A portion of $X_p(t)$ that is less than the boundary onset threshold of TO(60%) at 731 may be mapped to numerical code 0, and a portion of $X_p(t)$ that is equal to or greater than the boundary onset threshold of TO(100%) at 734 may be mapped to numerical code 20.

Figure 8:
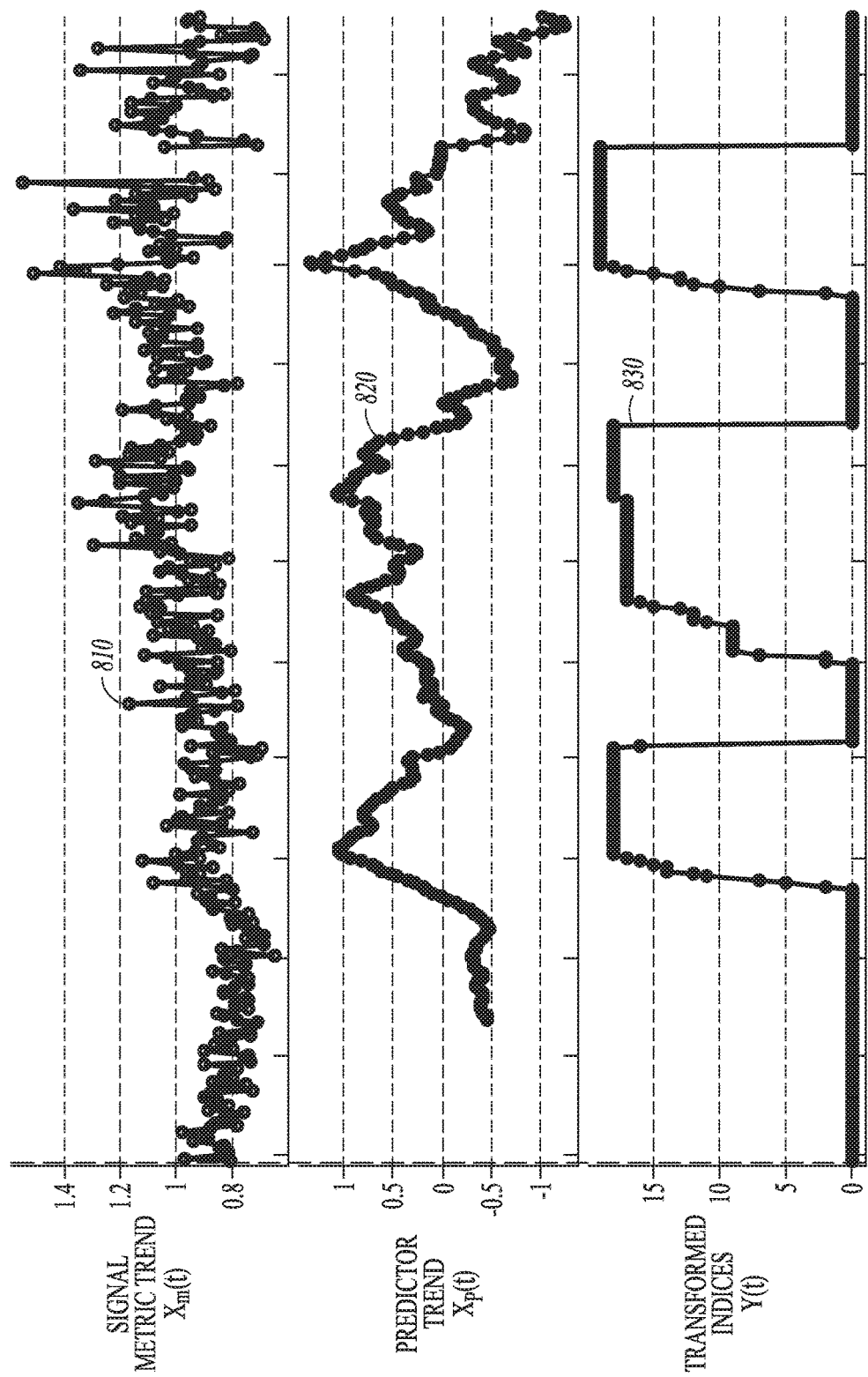
FIG. 8 illustrates generally an example of a transformation of a predictor trend.

FIG. 8 illustrates generally an example of a transformation of a predictor trend 820. The predictor trend 820, $X_p(t)$, may be produced using the signal metric trend 810, $X_m(t)$ such as by the predictor trend generator circuit 222. In an example, the signal metric trend 810 may be a trend of daily physiological measurements over a specified period of time, such as thoracic impedance measurements, S3 heart sound intensity measurements, normalized S3 heart sound intensity measurements, pressure measurements, heart sounds timing interval measurements, respiration rate measurements, tidal volume measurements, respiration rate and tidal volume ratio measurements, minute ventilation measurements, heart rate measurements, physical activity level measurements, posture measurements, or time of being physically active measurements. In an example, the predictor trend 820 may be generated such that each data point of the predictor trend 820 at a time T is computed as a difference between a short-term average of $X_m(t)$ over a first plurality of days up to the time T and a long-term average, which may represent a baseline value of $X_m(t)$, over a second plurality of days preceding the first plurality of days in time. The predictor trend 820 may be transformed into a plurality of indices 830, Y(t), such as by the signal transformation circuit 224. The transformation may be according to the codebook 427 based on the ROC sampling, or according to the codebook 627 based on cSID sampling, as previously discussed with reference to FIGS. 4-7. The transformed indices 830 take values between 0 and 20, and have the same data length as, and preserve the timings of, the predictor trend $X_p(t)$. The detector circuit 230 may use the transformed indices 830 to determine presence of a target physiological event, such as a WHF event, such as in response to the transformed indices 830 exceeds a detection threshold or falls within a specified range.

Figure 9:
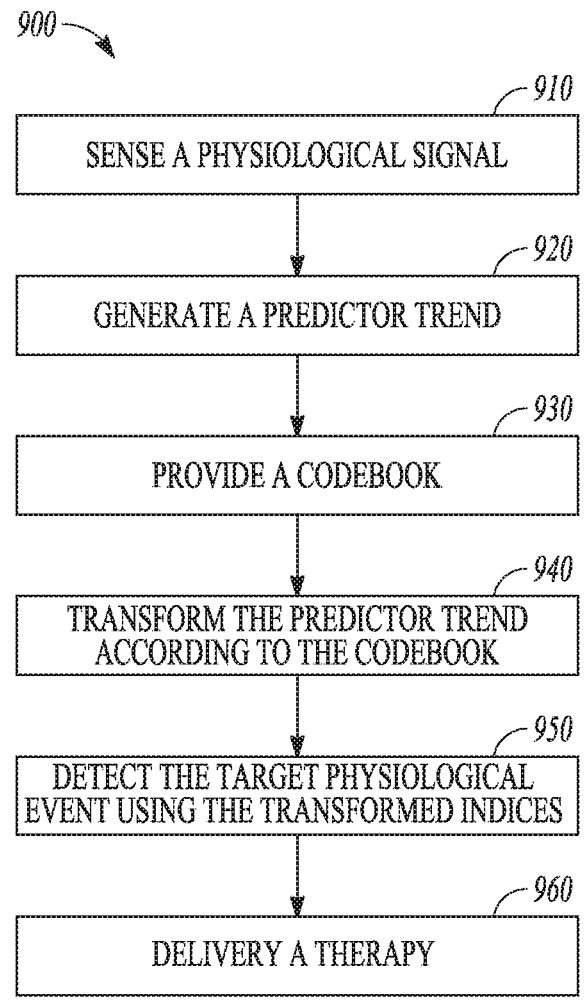
FIG. 9 illustrates generally an example of a method for detecting a target physiological event from a patient.

FIG. 9 illustrates generally an example of a method 900 for detecting a target physiological event from a patient. The target physiological event may include a worsening heart failure (WHF) event such as a HF decompensation event, or an event indicative of recovery from a HF condition. The method 900 may be implemented and operate in an ambulatory medical device such as an implantable or wearable medical device, or in a remote patient management system. In an example, the method 900 may be performed by the worsening cardiac condition detector 113 or any embodiment thereof, or by the external system 120.

The method 900 begins at 910 by sensing at least one physiological signal from a patient. Examples of the physiological signal may include one or more of an electrocardiograph (ECG) or electrogram (EGM) such as sensed from electrodes on one or more of the leads 108A-C or the can housing 112, an impedance signal, an arterial pressure signal, a pulmonary artery pressure signal, an RV pressure signal, an LV coronary pressure signal, a coronary blood temperature signal, a blood oxygen saturation signal, a heart sound (HS) signal, or a respiration signal rate signal or a tidal volume signal, among others. In an example, a thoracic or cardiac impedance signal may be sensed according a specified impedance vector that includes one or more electrodes on one or more of the implantable leads such as 108A-C or the can housing 112 implanted or otherwise attached to the patient. The impedance may be sensed in response to a detection of a triggering event such as a change of a physiological state, a change of the patient's health condition, or a specific time of a day such as when the patient is awake.

The sensed impedance may be pre-processed, including one or more of signal amplification, digitization, filtering, or other signal conditioning operations. One or more statistical or morphological signal metrics may be extracted from the pre-processed signal. Examples of the signal metrics may include thoracic impedance magnitude, S3 heart sound intensity, a ratio of S3 heart sound intensity to a reference heart sound intensity (such as S1 heart sound intensity, heart sound signal energy between R-wave and S2, or heart sound signal energy within a cardiac cycle), a heart sound timing interval, a pressure, a respiration rate, a tidal volume, a ratio a respiration rate to a tidal volume, a minute ventilation, an activity intensity, a posture, or a time duration when the activity intensity is within a specified range or above a specified threshold, among others. Multiple measurements of the signal metric trend may be performed to form a signal metric trend $X_m(t)$, such as a daily trend including daily measurement of a signal metric over a specified number of days. In an example, the daily measurement may be determined as a central tendency of a plurality of measurements obtained within a day.

At 920, a predictor trend $X_p(t)$ may generate from the signal metric trend $X_m(t)$. The predictor trend $X_p(t)$ may indicate change of the physiological signal. The predictor trend $X_p(t)$ may be determined based on a comparison between a first portion of the signal metric trend $X_m(t)$ within a short-term time window and a second portion of the signal metric trend within a long-term time window longer in duration than the short-term window. In an example, the predictor trend may be determined as a relative difference between the short-term values and baseline values. The short-term value may include a statistical measure such as a central tendency of the measurements of the signal metric within the short-term time window. The baseline value may include a statistical measure such as a central tendency of the measurements of the signal metric within the long-term time window which is longer in duration than the short-term window.

At 930, a codebook may be provided, such as received from a user input via the user interface unit 250, or retrieved from the memory circuit 226 or other storage device such as an electronic medical record (EMR) system. The codebook may include an association between the plurality of threshold pairs $\{(TO_i, TR_i)\}$ and corresponding code words $\{C_i\}$. In an example, the threshold pairs $\{(TO_i,TR_i)\}$ may be mapped to the code words $\{C_i\}$. The code words $\{C_i\}$ may include numerical codes within a specified range. In an example, the numerical codes take values between 0 and 20. A threshold pair with a higher onset threshold or a higher reset threshold may be associated with a larger numerical code than a threshold pair with a lower onset threshold or a lower reset threshold. Table 1-3 illustrate non-limiting examples of the codebook that may be used for signal transformation. The codebook may be generated using a receiver operating characteristic (ROC) of a specified signal metric, or using a composite signal intensity distribution (cSID). Examples of generating a codebook, or updating an existing codebook, are discussed below, such as with reference to FIGS. 10-11.

At 940, the predictor trend $X_p(t)$ may be transformed into a plurality of transformed indices $Y(t)$ according to the codebook. The transformation may be a mapping that preserves timing of the predictor trend $X_p(t)$, such that the transformed indices $Y(t)$ have the same data length as, and correspond in time with, the predictor trend $X_p(t)$. In an example, the transformation may be an isometric transformation that preserves relative intensity of the predictor trend $X_p(t)$. To transform the $X_p(t)$ using the codebook, a relevant threshold pair $(TO_i, TR_i)$ may be identified from the codebook for a specified portion of the predictor trend $X_p(t)$. The specified portion of the $X_p(t)$ temporally occurs after the first threshold crossing where the $X_p(t)$ exceeds the $TO_i$, and prior to the second threshold crossing where $X_p(t)$ subsequently falls below the $TR_i$. The numerical code, $C(i)$, corresponding to the identified relevant threshold pair $(TO_i, TR_i)$ may then be assigned to the specified portion of the predictor trend $X_p(t)$, according to the codebook. In an example, the same numerical code $C(i)$ is assigned to all data samples of the specified portion of the $X_p(t)$.

In some examples, two or more relevant threshold pairs may be identified from the codebook for a specified portion of the predictor trend $X_p(t)$, such as the examples as illustrated in FIGS. 3A-B. A dominant threshold pair may be identified from the two or more relevant threshold pairs, where the dominant threshold has a larger onset threshold or a larger reset threshold than any other of the identified relevant threshold pairs. The numerical code associated with the dominant threshold pair may be assigned to the specified portion of the predictor trend.

At 950, the target physiological event may be detected from the transformed indices. The target physiological event may include an onset of a disease, worsening of a disease state, or a change of a disease state, such as a WHF event, pulmonary edema, pneumonia, or myocardial infarction, among others. In an example, the detection may include a comparison of the transformed indices $Y(t)$ to a specified threshold. The target physiological event is deemed detected if $Y(t)$ exceeds the specified threshold. In an example, an alert can be generated if $Y(t)$ exceeds a first threshold. The alert may sustain until $Y(t)$ falls below a second threshold indicating a recovery or improvement of the physiological status.

In some examples, the target physiological event may be detected using two or more signal metrics, such as a first signal metric trend $X1_m(t)$ from a first physiological signal and a second signal metric trend $X2_m(t)$ different from $X1_m(t)$ from the first physiological signal or a different second physiological signal. A first codebook may be used to transform the first predictor trend $X1_p(t)$ into first transformed indices $Y1(t)$, and a second codebook may be used to transform the second predictor trend $X2_p(t)$ into second transformed indices $Y2(t)$. The first and second codebooks may have the same code words such as numerical codes within a specified value range such as between 1 and 20 as illustrated in Tables 1 and 2. At 950, both the first and second transformed indices $Y1(t)$ and $Y2(t)$ are used to detect the target physiological event. In an example, a composite transformed indices such as a linear or a nonlinear combination of $Y1(t)$ and $Y(2)$ may be compared to a detection threshold to detect the target physiological event.

In an example, the codebook provided at 930 may include an association between a plurality of multi-dimensional threshold pairs and corresponding code words. The multi-dimensional threshold pairs such as $\{(TO1_i, TR1_i; TO2_i, TR2_i)\}$ may include a first threshold pair $(TO1_i, TR1_i)$ for the first predictor trend $X1_p(t)$ and a second threshold pair $(TO2_i, TR2_i)$ for the second predictor trend $X2_p(t)$. At 940, the first and second predictor trends $X1_p(t)$ and $X2_p(t)$ may be jointly transformed into transformed indices using a joint transformation, such as according to the codebook. At 950, the target physiological event may be detected using a joint transformation of two or more predictor trends $X1_p(t)$ and $X2_p(t)$.

The information about the detected target physiological event, or optionally along with one or more predictor trends or the transformed indices, may be presented to a clinician. The information may be presented in a table, a chart, a diagram, or any other types of textual, tabular, or graphical presentation formats, for displaying to a system user. The presentation of the output information may include audio or other human-perceptible media format to alert the system user of the detected progression of cardiac condition, such as when the transformed indices satisfies a detection criterion. Additionally or alternatively, as illustrated in FIG. 9, the method 900 may include a step 960 of delivering a therapy to the patient in response to the detection of the target physiological event or condition. Examples of the therapy may include electrostimulation therapy delivered to the heart, a nerve tissue, other target tissues in response to the detection of the target physiological event, or drug therapy including delivering drug to a tissue or organ. In some examples, at 960 an existing therapy may be modified, such as adjusting a stimulation parameter or drug dosage.

Figure 10:
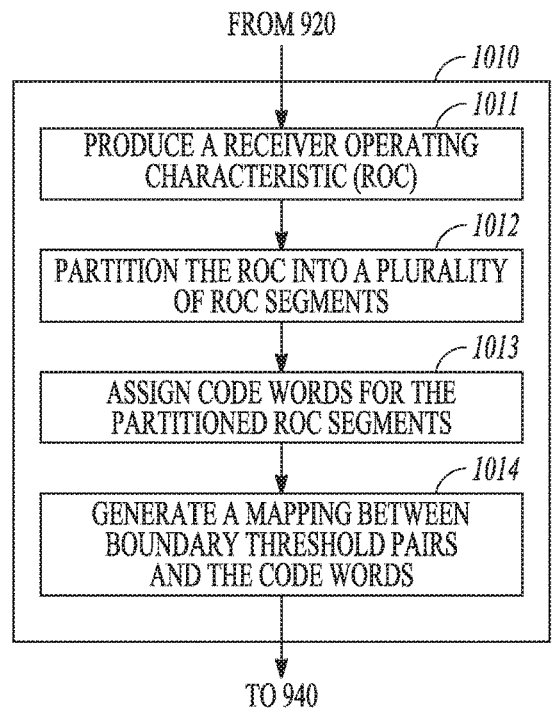
FIG. 10 illustrates the method for generating the codebook using an ROC of a specified signal metric.
Figure 11:
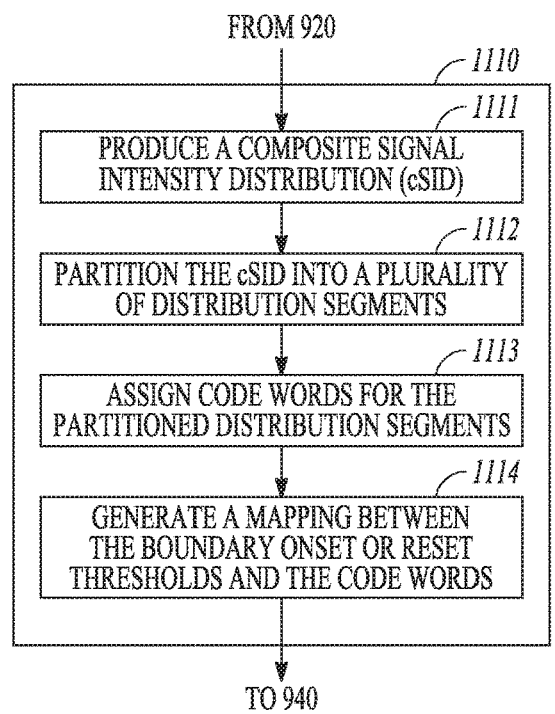
FIG. 11 illustrates the method for generating the codebook using a composite signal intensity distribution (cSID).

FIGS. 10 and 11 illustrate different methods for generating a codebook for transforming a predictor trend into transformed indices. The codebook may be generated using a receiver operating characteristic (ROC) of a specified signal metric, as illustrated in a method 1010 in FIG. 10, or using a composite signal intensity distribution (cSID) as illustrated in a method 1110 in FIG. 11. The methods 1010 and 1110 may be embodiments of step 930 of the method 900. The codebook generated using the methods 1010 or 1110 may be provided at 930, or may be used to update the existing codebook stored in the memory circuit 226, 426, or 626, or an EMR system.

The method 1010 illustrated in FIG. 10 may be implemented in and executed by the codebook formation/update circuit 460 in FIG. 4. The method 1010 begins at 1011 by producing a ROC using signal metric trends collected from a selected cohort of patients (such as CHF patients with risks of developing WHF events). The ROC may comprise a plurality of operating points indicating sensitivity statistics and false positive rate (FPR) statistics associated with a plurality of candidate threshold pairs, and may thus be used to describe a performance of a detector or a detection algorithm. The ROC may be produced using the detections of the target physiological event according to a plurality of candidate threshold pairs and annotations of the signal metric trends including clinical decisions of presence or absence of the WHF event. The annotations may be provided by clinicians and stored in the memory circuit 426.

At 1012, the ROC may be partitioned into a plurality of ROC segments defined by boundary operating points associated with respective boundary threshold pairs. Each ROC segment is associated with a sensitivity statistics range, a FPR statistics range, and a range of onset and reset thresholds. As previously discussed with reference to FIG. 5A-C, the portioning of the ROC may include sampling one of the FPR statistics, the sensitivity statistics, or the ROC curve that connects the plurality of operating points in a two-dimensional ROC plane spanned by the sensitivity statistics in the y-axis and the FPR statistics in the x-axis. In an example, the FPR statistics within a specified FPR range may be sampled at specified sampling intervals, such as a linear sampling that produces a plurality of intermediate FPRs. In another example, the sensitivity statistics (SENS) of the ROC curve may be sampled within a specified sensitivity range at specified sampling intervals such as to produce a plurality of intermediate sensitivities. In yet another example, a portion of the ROC curve, such as a specified portion of the operation points within a specified sensitivity range and a specified FPR range, may be sampled at specified sampling intervals such as to produce a plurality of intermediate boundary operating points. The sampling may be performed such that the boundary operating points are equally spaced along the ROC curve according to a distance measure such as a Euclidean distance.

At 1013, respective code words may be assigned for the partitioned ROC segments defined by the boundary operating points on the ROC curve. A mapping between the boundary threshold pairs and the code words may be established at 1014. For example, the FPRs and the sensitivities corresponding to the boundary operating points on the ROC curve may be associated with respective boundary threshold pairs, and a codebook may be generated by establishing an association between the boundary threshold pairs for the boundary operating points and the code words. The code words may be numerical codes, and a boundary threshold pair associated with an operating point with a lower sensitivity or a lower FPR may be mapped to a higher numerical code. The resultant codebook may be used at 940 of the method 900 for transforming the predictor trend.

The method 1110 illustrated in FIG. 11 may be implemented in and executed by the codebook formation/update circuit 660 in FIG. 6. The method 1110 begins at 1111 by producing a cSID using a plurality of predictor trends pertaining to a specified signal metric, collected from a selected cohort of patients such as CHF patients with risks of developing WHF events. The cSID may include a histogram with percentile frequencies of the magnitude of the predictor trends across a number of magnitude bins. Each magnitude bin may be defined by boundary candidate onset and reset thresholds. In an example, the histogram may be interpolated, extrapolated, or smoothened to produce a continuous distribution function.

At 1112, the cSID may be partitioned into a plurality of distribution segments defined by percentile frequency thresholds (PFTs) associated with respective boundary onset or reset thresholds. As previously discussed with reference to FIG. 7A, the partitioning of the cSID may include sampling the candidate onset or reset thresholds within a specified threshold range at specified sampling intervals to produce boundary onset or reset thresholds, or sampling the percentile frequencies within a specified percentile frequency range at specified sampling intervals to produce boundary percentile frequencies. In an example, a linear sampling of the candidate onset or reset thresholds may be performed to produce boundary thresholds uniformly distributed within the specified threshold range. Similarly, a linear sampling of the percentile frequencies may be performed to produce boundary percentile frequencies uniformly distributed within the specified frequency range.

Partitioning of cSID may alternatively include a piecewise linear sampling of the percentile frequency range or the onset or resent threshold range. One or more anchor percentile frequencies (APF) may be specified, each representing the percentage of signal magnitude of the predictor trends that falls below the corresponding onset or reset threshold. Each APF corresponds to an onset or reset threshold. A higher APF may correspond to a higher onset or reset threshold. The onset or reset thresholds corresponding to the APFs may be used to partition the onset or reset threshold range into two or more segments. As previously discussed in an example with reference to FIG. 7B, each segment defined by adjacent boundary onset thresholds may be linearly sampled at a specified sampling interval to generate intermediate boundary onset thresholds. In an example, each boundary onset thresholds corresponding to the APFs may be assigned a corresponding user-specified code word, such as $C(APF_1)$ for the boundary onset threshold $TO(APF_1)$, and $C(APF_2)$ for the boundary onset threshold $TO(APF_2)$. By piece-wise linear sampling, the segment between $TO(APF_1)$ and $TO(APF_2)$ may be sampled at a sampling interval determined by $[TO(APF_2)-TO(APF_1)]/[C(APF_2)$ and $C(APF_1)]$, such that the code words between $C(APF_1)$ and $C(APF_2)$ are evenly distributed between $TO(APF_1)$ and $TO(APF_2)$.

At 1113, respective code words may be assigned for the partitioned cSID segments defined by the boundary onset or reset thresholds. A mapping between the boundary onset or reset threshold and the code words may be established at 1114, such as the codebook shown in Table 2. The codebook may alternatively include an association between the percentile frequency thresholds (which correspond to the boundary onset thresholds) and the code words, such as the codebook shown in Table 3. In some examples, the boundary reset thresholds may be determined as a linear or nonlinear function of the boundary onset thresholds, and the codebook may include an association between the boundary threshold pairs $\{(TO_i, TR_i)\}$ and the corresponding code words. The resultant codebook may be used at 940 of the method 900 for transforming the predictor trend. In an example, a portion of the predictor trend that falls between the onset thresholds $TO(PF_i)$ and $TO(PF_{i+1})$ may be mapped to the numerical code corresponding to the onset threshold $TO(PF_i)$.

The above detailed description includes references to the accompanying drawings, which form a part of the detailed description. The drawings show, by way of illustration, specific embodiments in which the disclosure may be practiced. These embodiments are also referred to herein as "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments may be combined with each other in various combinations or permutations. The scope of the disclosure should be determined with reference to the appended claims, along with the full scope of equivalents to which such claims are entitled.

What is claimed is:

1. A system for detecting a target physiological event, the system comprising:
    a physiological sensor circuit including a sense amplifier circuit to sense a first physiological signal;
    a signal processor circuit coupled to the physiological sensor circuit, the signal processor circuit including:
        a predictor circuit configured to generate a first predictor trend using the first physiological signal, the first predictor trend indicating a change of the first physiological signal over time; and
        a signal transformation circuit configured to transform the first predictor trend into transformed indices using a comparison of the first predictor trend to a first plurality of threshold pairs each including an onset threshold and a reset threshold; and
    a detector circuit coupled to the signal processor circuit, the detector circuit configured to detect the target physiological event using the transformed indices; and
    an output circuit configured to generate a human-perceptible alert in response to the transformed indices satisfying a detection criterion.

2. The system of claim 1, further comprising a therapy circuit configured to deliver a therapy in response to the detection of the target physiological event.

3. The system of claim 1, wherein the signal transformation circuit is to transform the first predictor trend using a codebook including an association between the first plurality of threshold pairs and corresponding code words,
    wherein the transformation of the first predictor trend using the codebook includes, for a specified portion of the first predictor trend:
    identifying from the codebook a relevant threshold pair with corresponding onset and reset thresholds, the specified portion temporally occurring after the first predictor trend exceeding the corresponding onset threshold and prior to the first predictor trend subsequently falling below the reset threshold; and
    assigning a numerical code corresponding to the identified relevant threshold pair to the specified portion of the first predictor trend.

4. The system of claim 3, wherein the signal transformation circuit is further configured to:

identify from the codebook two or more relevant threshold pairs for the specified portion of the first predictor trend;

determine a dominant threshold pair from the two or more relevant threshold pairs, the dominant threshold pair having a larger onset threshold or a larger reset threshold than any other of the identified relevant threshold pairs; and assign a numerical code corresponding to the dominant threshold pair to the specified portion of the first predictor trend.

5. The system of claim 3, further comprising a codebook formation circuit configured to:

produce a receiver operating characteristic (ROC) using detections of the target physiological event according to a plurality of candidate threshold pairs and, the ROC including operating points indicating sensitivity statistics and false positive rate (FPR) statistics associated with the plurality of candidate threshold pairs;

partition the ROC into a plurality of ROC segments defined by boundary operating points associated with respective boundary threshold pairs;

assign code words for the partitioned ROC segments; and generate the codebook including the mapping between the boundary threshold pairs and the code words.

6. The system of claim 5, wherein the codebook formation circuit is configured to partition the ROC including one of:

sample the FPR statistics within a specified FPR range at specified sampling intervals;

sample the sensitivity statistics within a specified sensitivity range at specified sampling intervals; or sample a specified portion of the operation points within a specified sensitivity range and a specified FPR range at specified sampling intervals.

7. The system of claim 6, wherein the codebook formation circuit is configured to sample from the specified portion of the operation points a specified number of operating points equally spaced along the specified portion of the operation points according to a distance measure.

8. The system of claim 3, wherein the signal transformation circuit is configured to produce a signal intensity distribution (SID) of the first predictor trend, and to transform the first predictor trend using the codebook and the SID of the first predictor trend, wherein the SID represents percentile frequencies of the first predictor trend across a plurality of candidate onset or reset thresholds; and wherein the codebook includes an association between the first plurality of threshold pairs including a plurality of percentile frequency thresholds (PFTs) and corresponding code words.

9. The system of claim 3, further comprising a codebook formation circuit configured to:

receive a plurality of first predictor trends from a plurality of patients;

produce a composite signal intensity distribution (cSID) of the plurality of first predictor trends, the cSID representing percentile frequencies across plurality of candidate onset or reset thresholds;

partition the cSID into a plurality of distribution segments defined by boundary percentile frequencies associated with respective boundary onset or reset thresholds;

assign code words for the partitioned distribution segments; and generate the codebook including the mapping between the boundary onset or reset thresholds and the code words.

10. The system of claim 9, wherein the codebook formation circuit is configured to partition the cSID including one of:

sample the candidate onset or reset thresholds within a specified threshold range at specified sampling intervals; or sample the percentile frequencies within a specified percentile frequency range at specified sampling intervals.

11. The system of claim 9, wherein the codebook formation circuit is configured to partition the cSID including:

receive one or more anchor percentile frequencies (APFs); and partition the cSID into a plurality of distribution segments using the APFs, the partitioned distribution segments associated with respective percentile frequency ranges and onset or rest threshold ranges; and sample the candidate onset or reset thresholds within each of the onset or reset threshold range.

12. The system of claim 1, wherein:

the physiological sensor circuit is to sense a second physiological signal;

the predictor circuit is to generate a second predictor trend different from the first predictor trend using the second physiological signal;

the signal transformation circuit is to transform the first and second predictor trends jointly into the transformed indices according to a codebook, the codebook including an association between a plurality of multi-dimensional thresholds and a plurality of code words, each multi-dimensional threshold including a first threshold pair for the first predictor trend and a second threshold pair for the second predictor trend; and the detector circuit is configured to detect the target physiological event using the transformed indices.

13. A method for detecting a target physiological event, the method comprising:

sensing a first physiological signal;

processing the first physiological signal to generate a first predictor trend indicating a change of the first physiological signal over time;

transforming the first predictor trend into transformed indices using a comparison of the first predictor trend to a first plurality of threshold pairs each including an onset threshold and a reset threshold;

detecting the target physiological event using the transformed indices; and generating a human-perceptible alert in response to the transformed indices satisfying a detection criterion.

14. The method of claim 13, wherein transforming the first predictor trend includes, for a specified portion of the first predictor trend:

identifying from a codebook a relevant threshold pair with corresponding onset and reset thresholds, the specified portion temporally occurring after the first predictor trend exceeding the corresponding onset threshold and prior to the first predictor trend subsequently falling below the reset threshold; and assigning a numerical code corresponding to the identified relevant threshold pair to the specified portion of the first predictor trend, wherein the codebook includes an association between the first plurality of threshold pairs and corresponding code words, the code words including numerical codes within a specified range.

15. The method of claim 14, wherein transforming the first predictor trend further includes, for the specified portion of the first predictor trend:

identifying from the codebook two or more relevant threshold pairs;

determining from the two or more relevant threshold pairs a dominant threshold pair having a larger onset threshold or a larger reset threshold than any other of the identified relevant threshold pairs; and assigning a numerical code corresponding to the dominant threshold pair to the specified portion of the first predictor trend.

16. The method of claim 14, further comprising generating a codebook, the generation of the codebook including:

producing a receiver operating characteristic (ROC) using detections of the target physiological event according to a plurality of candidate threshold pairs, the ROC including operating points indicating sensitivity statistics and false positive rate (FPR) statistics associated with the plurality of candidate threshold pairs;

partitioning the ROC into a plurality of ROC segments defined by boundary operating points associated with respective boundary threshold pairs;

assigning code words for the partitioned ROC segments; and generating a mapping between the boundary threshold pairs and the code words.

17. The method of claim 16, wherein partitioning the ROC includes one of:

sampling the FPR statistics within a specified FPR range at specified sampling intervals;

sampling the sensitivity statistics within a specified sensitivity range at specified sampling intervals; or sampling a specified portion of the operation points within a specified sensitivity range and a specified FPR range at specified sampling intervals.

18. The method of claim 14, further comprising generating a codebook, the generation of the codebook including:

producing a composite signal intensity distribution (cSID) using a plurality of first predictor trends from a plurality of patients, the cSID representing percentile frequencies across plurality of candidate onset or reset thresholds;

partitioning the cSID into a plurality of distribution segments defined by boundary percentile frequencies associated with respective boundary onset or reset thresholds;

assigning code words for the partitioned distribution segments; and generating a mapping between the boundary onset or reset thresholds and the code words.

19. The method of claim 18, wherein partitioning the cSID includes one of:

sampling the candidate onset or reset thresholds within a specified threshold range at specified sampling intervals; or sampling the percentile frequencies within a specified percentile frequency range at specified sampling intervals.

20. The method of claim 13, further comprising:

sensing a second physiological signal;

processing the second physiological signal to generate a second predictor trend different from the first predictor trend; and transforming the first and second predictor trends jointly into the transformed indices according to a codebook, the codebook including an association between a plurality of multi-dimensional thresholds and a plurality of code words, each multi-dimensional threshold including a first threshold pair for the first predictor trend and a second threshold pair for the second predictor trend; and wherein detecting the target physiological event includes detecting the target physiological event using the transformed indices.

* * * * *